(12) United States Patent
Chen et al.

(10) Patent No.: US 9,855,114 B2
(45) Date of Patent: Jan. 2, 2018

(54) METHOD AND SYSTEM FOR USER INTERACTION IN 3-D CEPHALOMETRIC ANALYSIS

(71) Applicant: Carestream Health, Inc., Rochester, NY (US)

(72) Inventors: Shoupu Chen, Rochester, NY (US); Jean-Marc Inglese, Bussy Saint Georges (FR); Lawrence A. Ray, Rochester, NY (US); Jacques Treil, Haut-Garonne (FR)

( * ) Notice: Subject to any disclaimer, the term of this patent is extended or adjusted under 35 U.S.C. 154(b) by 836 days.

(21) Appl. No.: 13/945,941

(22) Filed: Jul. 19, 2013

(65) Prior Publication Data
US 2014/0348405 A1    Nov. 27, 2014

Related U.S. Application Data

(60) Provisional application No. 61/825,548, filed on May 21, 2013.

(51) Int. Cl.
*G06K 9/00*    (2006.01)
*A61C 7/00*    (2006.01)
(Continued)

(52) U.S. Cl.
CPC ............... *A61C 7/002* (2013.01); *G06T 7/60* (2013.01); *G06T 7/75* (2017.01);
(Continued)

(58) Field of Classification Search
USPC ............... 1/1; 340/988; 345/419, 441, 634; 348/42; 382/118, 154; 433/24; 434/263
See application file for complete search history.

(56) References Cited

U.S. PATENT DOCUMENTS 5,448,694 A * 9/1995 Wada ..................... G06T 13/00
                                                    345/441
5,951,498 A * 9/1999 Arnett ..................... A61C 7/00
                                                    600/587

(Continued)

FOREIGN PATENT DOCUMENTS

WO    2010135790    12/2010

OTHER PUBLICATIONS

Forsyth, D. B. and Davis, D. N. "Assessment of an automated cephalometric analysis system," European Journal of Orthodontics, 1996, 18(5):471-478.*

(Continued)

*Primary Examiner* — Xuemei Chen
(74) *Attorney, Agent, or Firm* — Thompson Hine LLP

(57) ABSTRACT

A method for 3-D cephalometric analysis acquires reconstructed volume image data from a computed tomographic scan of a patient's head. The acquired volume image data simultaneously displays from at least a first 2-D view and a second 2-D view. For an anatomical feature of the head, an operator instruction positions a reference mark corresponding to the feature on either the first or the second displayed 2-D view and the reference mark displays on each of the at least first and second displayed 2-D views. In at least the first and second displayed 2-D views, one or more connecting lines display between two or more of the positioned reference marks. One or more cephalometric parameters are derived according to the positioned reference marks, the derived parameters are displayed.

20 Claims, 32 Drawing Sheets

(51) Int. Cl.
*G06T 7/60* (2017.01)
*G06T 7/73* (2017.01)

(52) U.S. Cl.
CPC ........... *G06T 2207/10081* (2013.01); *G06T 2207/20101* (2013.01); *G06T 2207/30016* (2013.01); *G06T 2207/30036* (2013.01)

(56) References Cited

U.S. PATENT DOCUMENTS

| | | | |
|---|---|---|---|
| 6,250,918 B1 | 6/2001 | Sachdeva et al. | |
| 6,832,139 B2* | 12/2004 | Johnson | G05D 1/0236 340/988 |
| 6,845,175 B2* | 1/2005 | Kopelman | A61B 6/14 128/922 |
| 6,879,712 B2 | 4/2005 | Tuncay et al. | |
| 6,888,546 B1* | 5/2005 | Kim | A61B 6/032 345/419 |
| 7,133,042 B2* | 11/2006 | Anh | G06T 17/10 345/419 |
| 7,463,757 B2* | 12/2008 | Luo | G01J 3/50 382/128 |
| 7,792,341 B2 | 9/2010 | Schutyser | |
| 7,950,849 B2* | 5/2011 | Claus | A61B 6/583 378/18 |
| 8,021,147 B2* | 9/2011 | Sporbert | A61C 7/00 433/24 |
| 8,023,706 B2* | 9/2011 | Witte | G06F 19/3437 128/922 |
| 8,142,187 B2* | 3/2012 | Sporbert | A61C 7/00 433/24 |
| 8,665,268 B2* | 3/2014 | Baker | G06T 19/00 345/420 |
| 8,761,493 B2* | 6/2014 | Chen | G06T 7/0081 348/42 |
| 8,805,048 B2* | 8/2014 | Batesole | A61C 7/00 345/634 |
| 8,842,904 B2* | 9/2014 | Chen | G06K 9/34 382/154 |
| 8,849,016 B2* | 9/2014 | Chen | G06T 3/4038 382/154 |
| 8,923,581 B2* | 12/2014 | Souza | G06T 7/11 382/128 |
| 8,929,635 B2* | 1/2015 | Chen | G06K 9/34 382/128 |
| 8,970,581 B2* | 3/2015 | Shi | G06T 7/11 345/419 |
| 9,153,022 B2* | 10/2015 | Finkelstein | A61B 5/1075 |
| 2007/0274440 A1* | 11/2007 | Sarment | G06T 7/0012 378/38 |
| 2011/0244415 A1 | 10/2011 | Batesole | |
| 2013/0022252 A1 | 1/2013 | Chen et al. | |
| 2013/0022254 A1 | 1/2013 | Chen et al. | |
| 2013/0022255 A1 | 1/2013 | Chen et al. | |
| 2013/0052625 A1* | 2/2013 | Wagner | A61C 13/34 434/263 |
| 2014/0270406 A1* | 9/2014 | George | G06K 9/00268 382/118 |

OTHER PUBLICATIONS

Ana Emilia F. de Oliveira, et al., "Observer reliability of three-dimensional cephalometric landmark identification on cone-beam computerized tomography," Oral Surger, Oral Medicine, Oral Pathology, Oral Radiology, and Endodontology, Oral and Maxillofacial Radiology, vol. 107, No. 2, Feb. 2009, pp. 256-265.

M. J. Troulis, et al., "Development of a three-dimensional treatment planning system based on computed tomographic data," Int. J. Oral Maxillofac. Surg., 2002; 31: pp. 349-357.

International Search Report dated Oct. 13, 2014 for International Application No. PCT/US2014/046461, 3 pages.

J. Treil et al., Tooth Modeling for Orthodontic Assessment, Seminars in Orthodontics, vol. 15, No. 1, Mar. 2009, pp. 42-47.

J. Treil et al., The Human Face as a 3D Model for Cephalometric Analysis, World Journal of Orthodontics, 2005, pp. 1-5.

P. Planche et al., Cephalometrics for the next millennium, The Future of Orthodontics, ed. Carine Cards, Leuven University Press, 1998, pp. 181-192.

Kumar et al., In Vivo Comparison of Conventional and Cone Beam CT Synthesized Cephalograms, Angle Orthodontics, Sep. 2008, pp. 873-879.

Cecil C. Steiner D.D.S., Cephalometrics in Clinical Practice (Read at the Charles H. Tweed Foundation for Orthodontic Research, Tucson, Arizona in Oct. 1956, pp. 8-29.

* cited by examiner

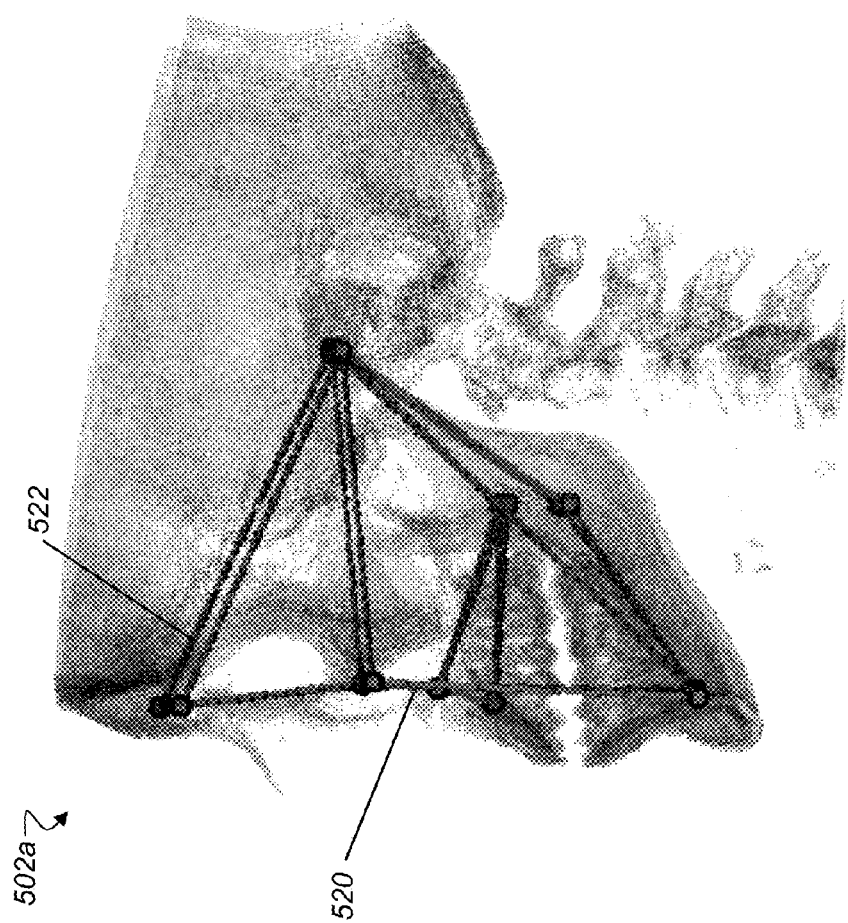

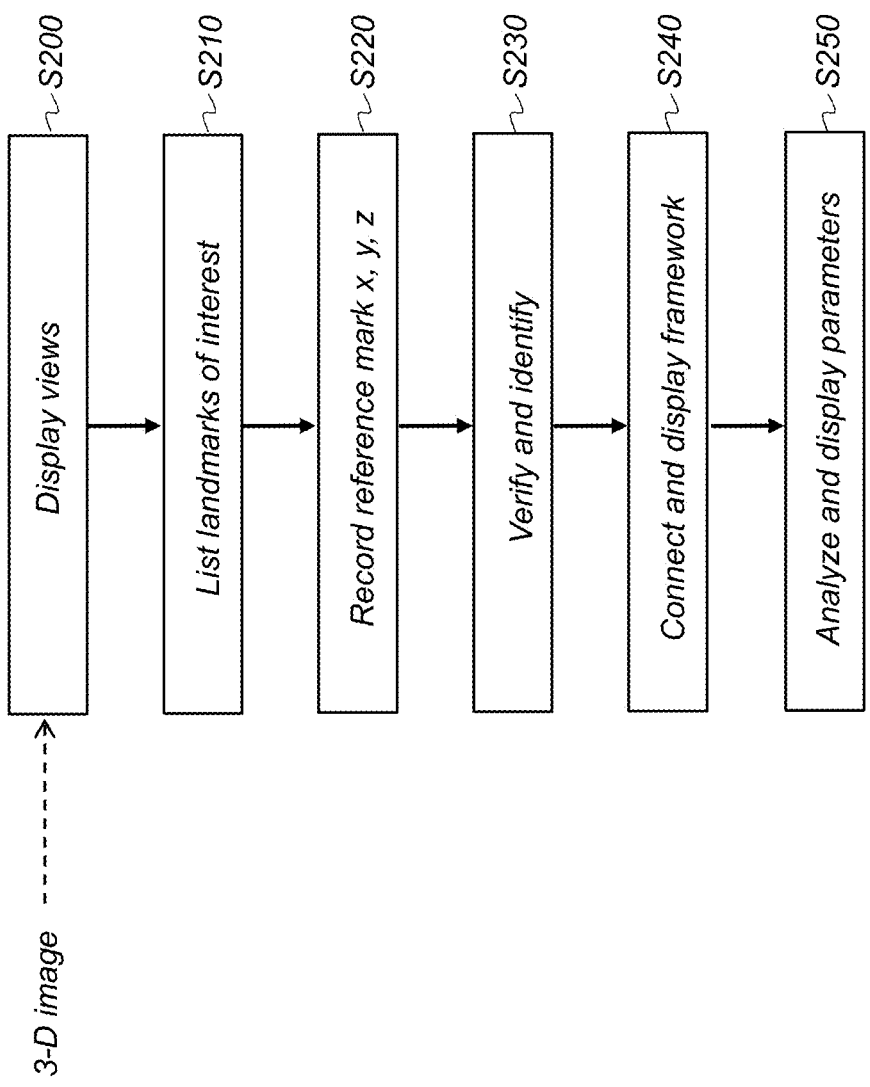

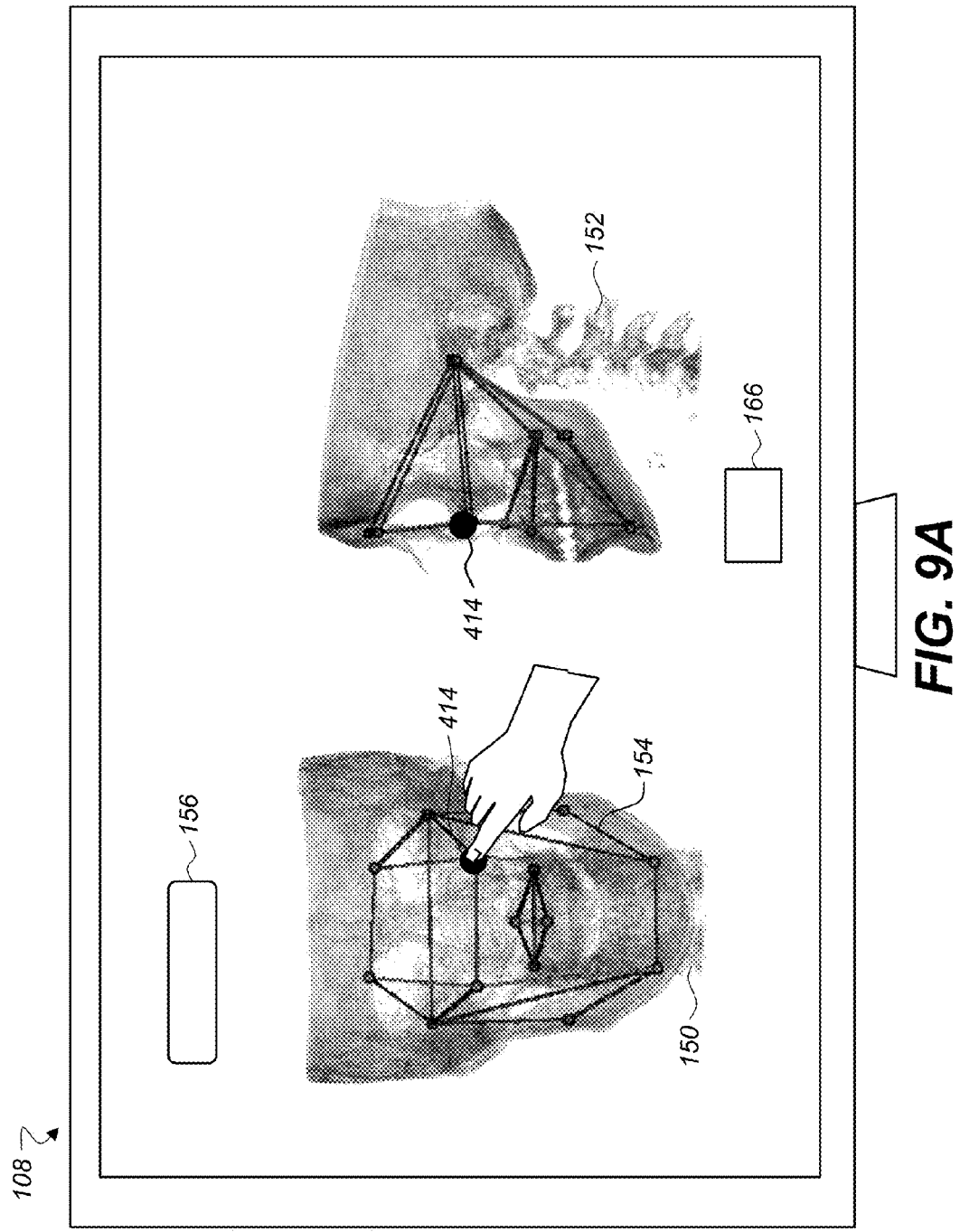

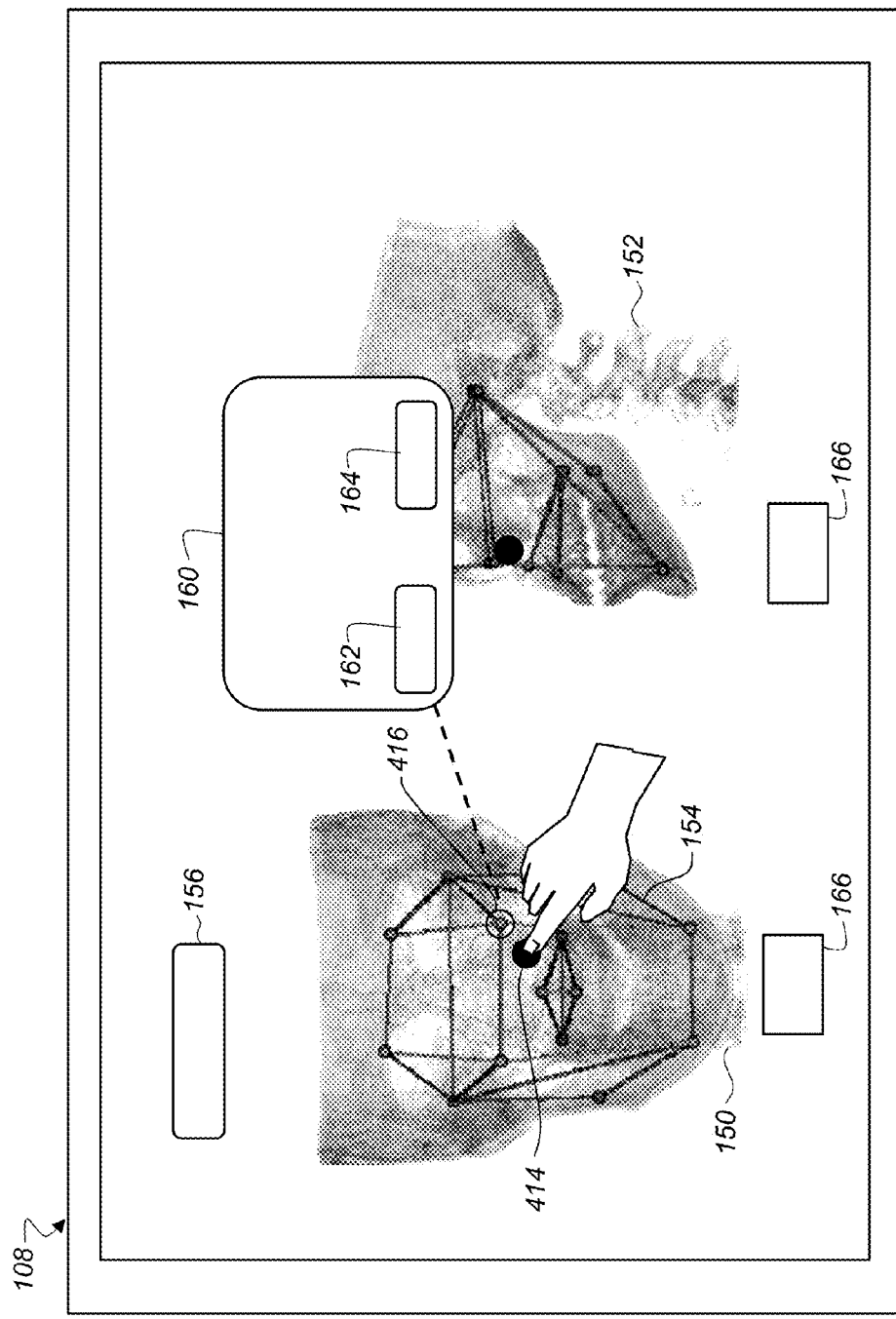

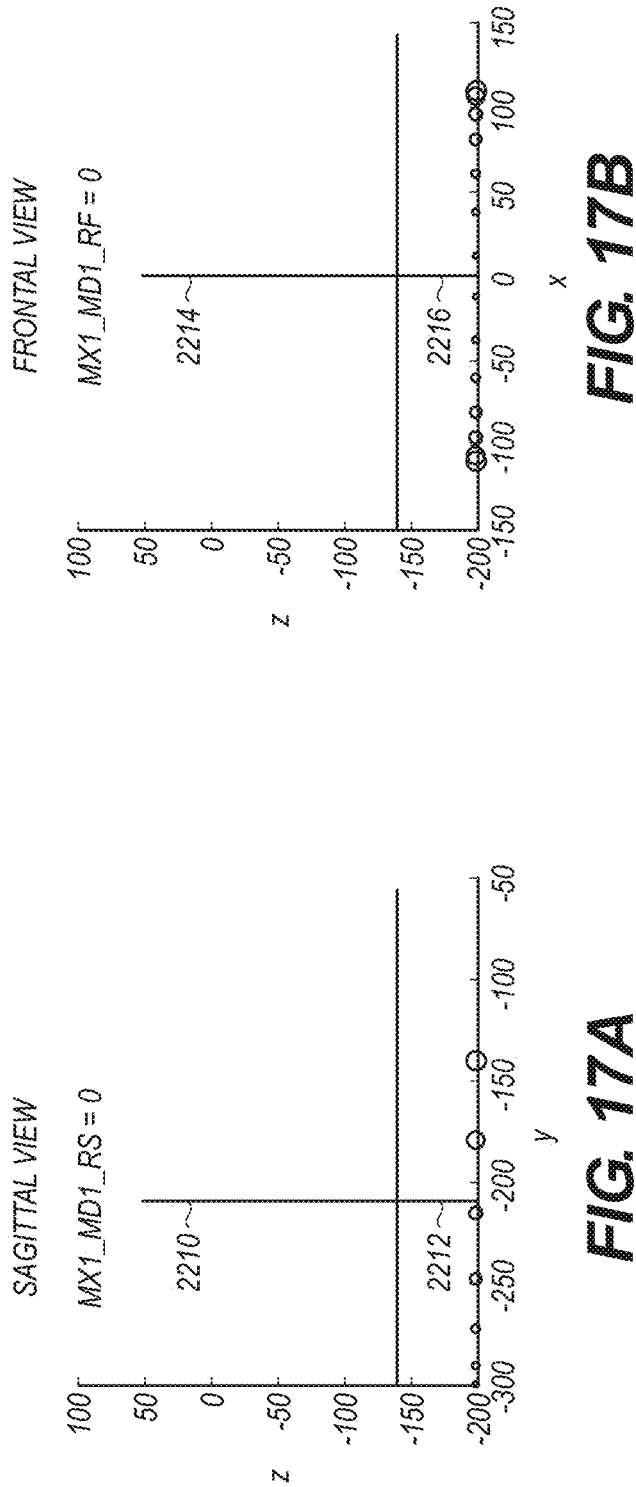

METHOD AND SYSTEM FOR USER INTERACTION IN 3-D CEPHALOMETRIC ANALYSIS

CROSS REFERENCE TO RELATED APPLICATIONS

This application claims the benefit of U.S. Provisional Patent Application Ser. No. 61/825,548 entitled "METHOD AND SYSTEM FOR USER INTERACTION IN 3-D CEPHALOMETRIC ANALYSIS" filed May 21, 2013 in the names of Chen et al., incorporated herein in its entirety by reference.

FIELD OF THE INVENTION

The present invention relates generally to image processing in x-ray computed tomography and, in particular, to acquiring 3-D data for three dimensional cephalometric analysis.

BACKGROUND OF THE INVENTION

Cephalometric analysis is the study of the dental and skeletal relationships for the head and is used by dentists and orthodontists as an assessment and planning tool for improved treatment of a patient. Conventional cephalometric analysis identifies bony and soft tissue landmarks in 2-D cephalometric radiographs in order to diagnose facial growth abnormalities prior to treatment, or to evaluate the progress of treatment.

An abnormality that can be identified in cephalometric analysis is the anteroposterior problem of malocclusion, relating to the skeletal relationship between the maxilla and mandible. Malocclusion is classified based on the relative position of the maxillary first molar. For Class I, neutrocclusion, the molar relationship is normal but other teeth may have problems such as spacing, crowding, or over- or under-eruption. For Class II, distocclusion, the mesiobuccal cusp of the maxillary first molar rests between the first mandible molar and second premolar. For Class III, mesiocclusion, the mesiobuccal cusp of the maxillary first molar is posterior to the mesiobuccal grooves of the mandibular first molar.

An exemplary conventional 2-D cephalometric analysis method described by Steiner in an article entitled "Cephalometrics in Clinical Practice" (paper read at the Charles H. Tweed Foundation for Orthodontic Research, October 1956, pp. 8-29) assesses maxilla and mandible in relation to the cranial base using angular measures. In the procedure described, Steiner selects four landmarks: Nasion, Point A, Point B and Sella. The Nasion is the intersection of the frontal bone and two nasal bones of the skull. Point A is regarded as the anterior limit of the apical base of the maxilla. Point B is regarded as the anterior limit of the apical base of the mandible. The Sella is at the mid point of the sella turcica. The angle SNA (from Sella to Nasion, then to Point A) is used to determine if the maxilla is positioned anteriorly or posteriorly to the cranial base; a reading of about 82 degrees is regarded as normal. The angle SNB (from Sella to Nasion then to Point B) is used to determine if the mandible is positioned anteriorly or posteriorly to the cranial base; a reading of about 80 degrees is regarded as normal.

Some studies in orthodontics indicate that there are inaccuracies and inconsistencies in results provided using conventional 2-D cephalometric analysis. One study is entitled "In vivo comparison of conventional and cone beam CT synthesized cephalograms" by Vandana Kumar et al. in *Angle Orthodontics*, September 2008, pp. 873-879.

Due to limitations in data acquisition, conventional 2-D cephalometric analysis is focused primarily on aesthetics, without the concern of balance and symmetry about the human face. As stated in an article entitled "The human face as a 3D model for cephalometric analysis" by Treil et al. in *World Journal of Orthodontics*, pp. 1-6, plane geometry is inappropriate for analyzing anatomical volumes and their growth; only a 3-D diagnosis is able to suitably analyze the anatomical maxillofacial complex. The normal relationship includes two aspects: balance and symmetry. When balance and symmetry of the model are stable, these characteristics define what is normal for each person.

U.S. Pat. No. 6,879,712 to Tuncay et al. discloses a method of generating a computer model of craniofacial features. The three-dimensional facial features data are acquired using laser scanning and digital photographs; dental features are acquired by physically modeling the teeth. The models are laser scanned. Skeletal features are then obtained from radiographs. The data are combined into a single computer model that can be manipulated and viewed in three dimensions. The model also has the ability for animation between the current modeled craniofacial features and theoretical craniofacial features.

U.S. Pat. No. 6,250,918 to Sachdeva et al. discloses a method of determining a 3-D direct path of movement from a 3-D digital model of an actual orthodontic structure and a 3-D model of a desired orthodontic structure. This method simulates tooth movement based on each tooth's corresponding three-dimensional direct path using laser scanned crown and markers on the tooth surface for scaling.

There is a need for a system and method that provide for interactively acquiring 3-D anatomical data for 3-D cephalometric analysis.

SUMMARY OF THE INVENTION

It is an object of the present invention to address the need for improved ways to acquire 3-D anatomical data for cephalometric analysis. With this object in mind, the present invention provides a method for 3-D cephalometric analysis, the method executed at least in part on a computer processor and comprising: acquiring reconstructed volume image data from a computed tomographic scan of a patient's head; simultaneously displaying the acquired volume image data from at least a first 2-D view and a second 2-D view; for each of a plurality of anatomical features of the head, (i) accepting an operator instruction that positions a reference mark corresponding to the feature on either the first or the second displayed 2-D view; (ii) displaying the reference mark on each of the at least first and second displayed 2-D views; displaying, in at least the first and second displayed 2-D views, one or more connecting lines between two or more of the positioned reference marks; deriving one or more cephalometric parameters according to the plurality of the positioned reference marks; and displaying at least one of the one or more derived parameters.

A feature of the present invention is interaction with an operator to identify the locations of reference marks indicative of anatomical features.

Embodiments of the present application, in a synergistic manner, integrate skills of a human operator of the system with computer capabilities for feature identification. This takes advantage of human skills of creativity, use of heuristics, flexibility, and judgment, and combines these with computer advantages, such as speed of computation, capability for exhaustive and accurate processing, and reporting and data access capabilities.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 7A, 7B, and 7C are perspective views that are projection images of a volume from a particular angle that show identified anatomical features that provide a framework for cephalometric analysis.

FIG. 8 is a logic flow diagram that shows steps for accepting operator instructions that generate the framework used for cephalometric analysis.

FIGS. 9A, 9B, and 9C show an operator interface for specifying the location of anatomical features using operator-entered reference marks on views that are projection images of a volume from a particular angle.

FIG. 17A is a graph showing parallelism for specific tooth structures.

FIG. 17B is a graph showing parallelism for specific tooth structures.

DETAILED DESCRIPTION OF THE INVENTION

Figure 1:
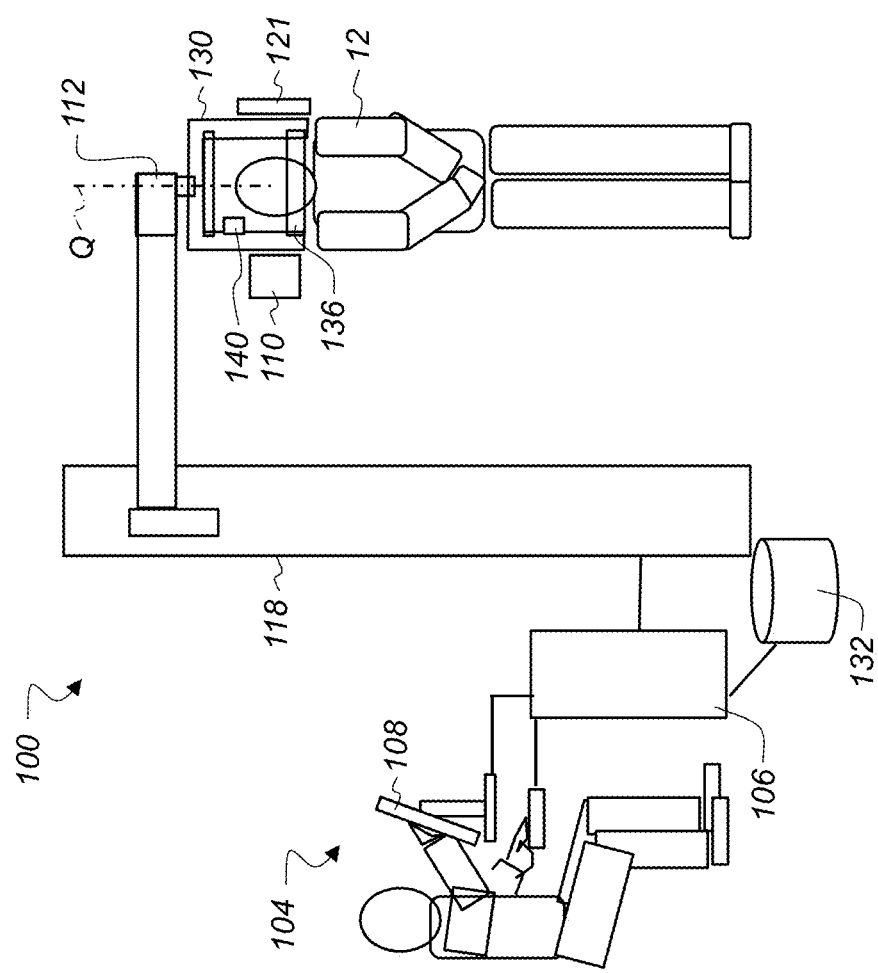
FIG. 1 is a schematic diagram showing an imaging system for providing cephalometric analysis.

In the following detailed description of embodiments of the present invention, reference is made to the drawings in which the same reference numerals are assigned to identical elements in successive figures. It should be noted that these figures are provided to illustrate overall functions and relationships according to embodiments of the present invention and are not provided with intent to represent actual size or scale.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2-D images, the discrete image elements are picture elements, or pixels. For 3-D images, the discrete image elements are volume image elements, or voxels. The term "volume image" is considered to be synonymous with the term "3-D image".

In the context of the present disclosure, the term "code value" refers to the value that is associated with each 2-D image pixel or, correspondingly, each volume image data element or voxel in the reconstructed 3-D volume image. The code values for computed tomography (CT) or cone-beam computed tomography (CBCT) images are often, but not always, expressed in Hounsfield units.

In the context of the present disclosure, the term "geometric primitive" relates to an open or closed shape such as a rectangle, circle, line, traced curve, or other traced pattern. The terms "landmark" and "anatomical feature" are considered to be equivalent and refer to specific features of patient anatomy as displayed.

In the context of the present disclosure, the terms "viewer", "operator", and "user" are considered to be equivalent and refer to the viewing practitioner or other person who views and manipulates an image, such as a dental image, on a display monitor. An "operator instruction" or "viewer instruction" is obtained from explicit commands entered by the viewer, such as using a computer mouse or touch screen or keyboard entry.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

In the context of the present invention, the descriptive term "derived parameters" relates to values calculated from processing of acquired or entered data values. Derived parameters may be a scalar, a point, a line, a volume, a vector, a plane, a curve, an angular value, an image, a closed contour, an area, a length, a matrix, a tensor, or a mathematical expression.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

In the context of the present disclosure, a "plan view" or "2-D view" is a 2-dimensional (2-D) representation or projection of a 3-dimensional (3-D) object from the position of a horizontal plane through the object. This term is synonymous with the term "image slice" that is conventionally used to describe displaying a 2-D planar representation from within 3-D volume image data from a particular perspective. 2-D views of the 3-D volume data are considered to be substantially orthogonal if the corresponding planes at which the views are taken are disposed at 90 (+/−10) degrees from each other, or at an integer multiple n of 90 degrees from each other (n*90 degrees, +/−10 degrees).

The subject matter of the present invention relates to digital image processing and computer vision technologies, which is understood to mean technologies that digitally process data from a digital image to recognize and thereby assign useful meaning to human-understandable objects, attributes or conditions, and then to utilize the results obtained in further processing of the digital image.

As noted earlier in the background section, conventional 2-D cephalometric analysis has a number of significant drawbacks. It is difficult to center the patient's head in the cephalostat or other measuring device, making reproducibility unlikely. The two dimensional radiographs that are obtained produce overlapped head anatomy images rather than 3-D images. Locating landmarks on cephalograms can be difficult and results are often inconsistent (see the article entitled "Cephalometrics for the next millennium" by P. Planche and J. Treil in *The Future of Orthodontics*, ed. Carine Carels, Guy Willems, Leuven University Press, 1998, pp. 181-192).

An embodiment can utilize Treil's theory in terms of the selection of 3-D anatomic feature points, parameters derived from these feature points, and the way to use these derived parameters in cephalometric analysis. Reference publications authored by Treil include "The Human Face as a 3D Model for Cephalometric Analysis" Jacques Treil, B, Waysenson, J. Braga and J. Casteigt in *World Journal of Orthodontics*, 2005 Supplement, Vol. 6, issue 5, pp. 33-38; and "3D Tooth Modeling for Orthodontic Assessment" by J. Treil, J. Braga, J.-M. Loubes, E. Maza, J.-M. Inglese, J. Casteigt, and B. Waysenson in *Seminars in Orthodontics*, Vol. 15, No. 1, March 2009.

The schematic diagram of FIG. 1 shows an imaging apparatus 100 for 3-D CBCT cephalometric imaging. For imaging a patient 12, a succession of multiple 2-D projection images is obtained and processed using imaging apparatus 100. A rotatable mount 130 is provided on a column 118, preferably adjustable in height to suit the size of patient 12. Mount 130 maintains x-ray source 110 and a radiation sensor 121 on opposite sides of the head of patient 12 and rotates to orbit source 110 and sensor 121 in a scan pattern about the head. Mount 130 rotates about an axis Q that corresponds to a central portion of the patient's head, so that components attached to mount 130 orbit the head. Sensor 121, a digital sensor, is coupled to mount 130, opposite x-ray source 110 that emits a radiation pattern suitable for CBCT volume imaging. An optional head support 136, such as a chin rest or bite element, provides stabilization of the patient's head during image acquisition. A computer 106 has an operator interface 104 and a display 108 for accepting operator commands and for display of volume images of the orthodontia image data obtained by imaging apparatus 100. Computer 106 is in signal communication with sensor 121 for obtaining image data and provides signals for control of source 110 and, optionally, for control of a rotational actuator 112 for mount 130 components. Computer 106 is also in signal communication with a memory 132 for storing image data. An optional alignment apparatus 140 is provided to assist in proper alignment of the patient's head for the imaging process.

Figure 2:
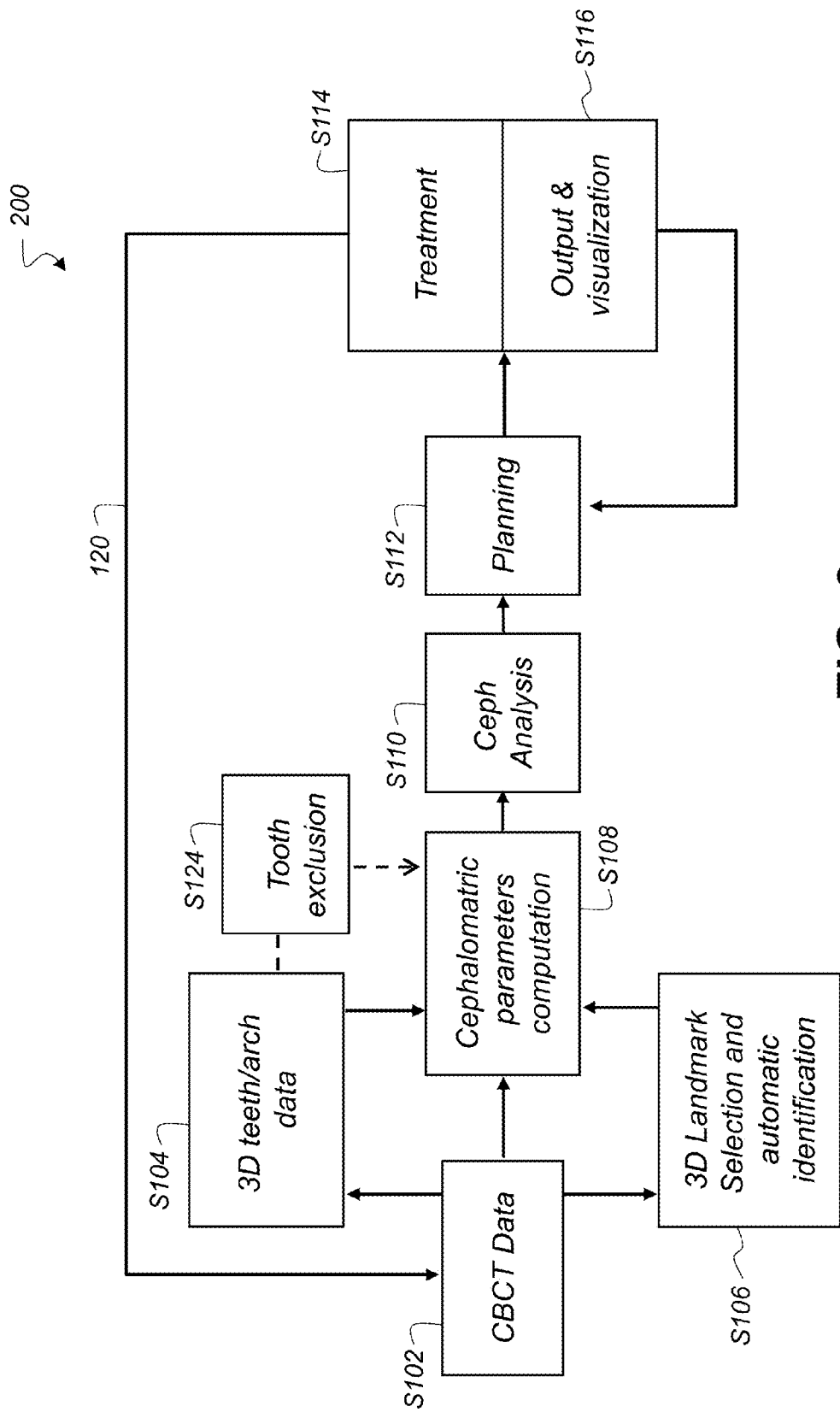
FIG. 2 is a logic flow diagram showing processes for 3-D cephalometric analysis according to an embodiment of the present invention.
Figure 3:
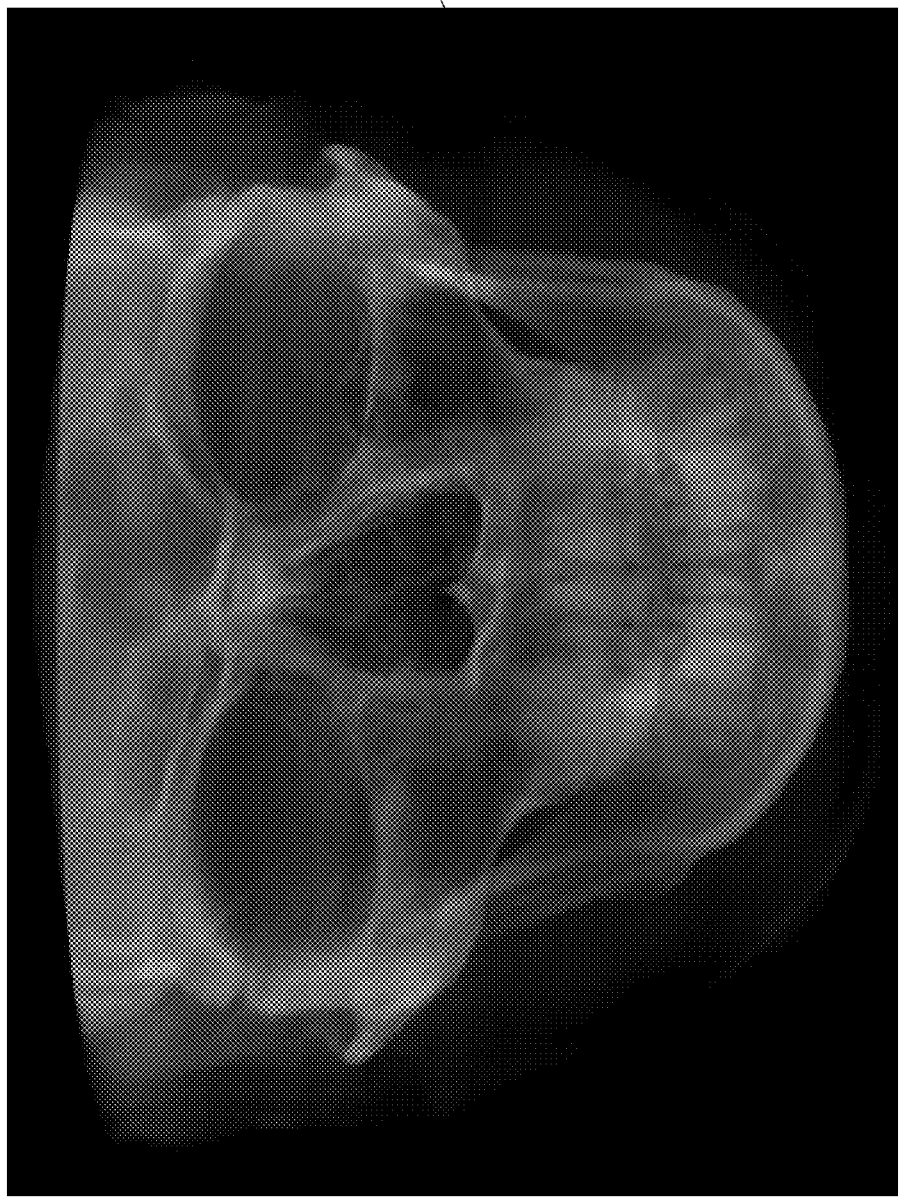
FIG. 3 is a view of 3-D rendered CBCT head volume images.

Referring to the logic flow diagram of FIG. 2, there is shown a sequence 200 of steps used for acquiring orthodontia data for 3-D cephalometric analysis with a dental CBCT volume according to an embodiment of the present invention. The CBCT volume image data is accessed in a data acquisition step S102. A volume contains image data for one or more 2-D images (or equivalently, slices). An original reconstructed CT volume is formed using standard reconstruction algorithms using multiple 2-D projections or sinograms obtained from a CT scanner. By way of example, FIG. 3 shows an exemplary dental CBCT volume 202 that contains bony anatomy, soft tissues, and teeth.

Continuing with the sequence of FIG. 2, in a segmentation step S104, 3-D teeth/arch data are collected by applying a 3-D teeth segmentation algorithm to the dental CBCT volume 202. Tooth segmentation algorithms are well known in the dental imaging arts. Exemplary tooth segmentation algorithms are described, for example, in commonly assigned U.S. 2013/0022252 entitled "PANORAMIC IMAGE GENERATION FROM CBCT DENTAL IMAGES" by Chen.; in U.S. 2013/0022255 entitled "METHOD AND SYSTEM FOR TOOTH SEGMENTATION IN DENTAL IMAGES" by Chen; and in U.S. 2013/0022254 entitled "METHOD FOR TOOTH DISSECTION IN CBCT VOLUME" by Chen, all of which are incorporated herein by reference in their entirety.

Figure 4:
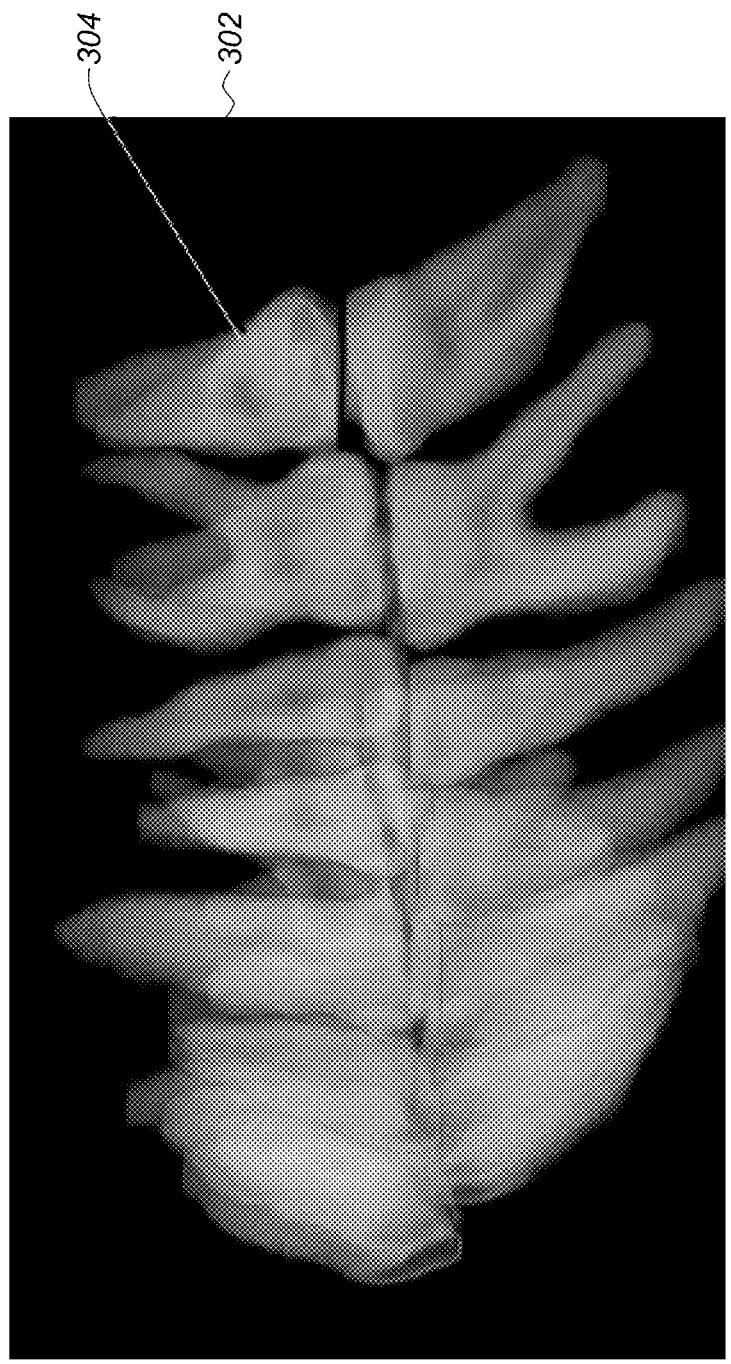
FIG. 4 is a view of a 3-D rendered teeth volume image after teeth segmentation.

Referring to FIG. 4, tooth segmentation results are rendered with an image 302, wherein teeth are rendered as a whole but are segmented individually. Each tooth is a separate entity called a tooth volume, for example, tooth volume 304.

Each tooth of the segmented teeth has, at a minimum, a 3-D position list that contains 3-D position coordinates for each of the voxels within the segmented tooth, and a code value list of each of the voxels within the segmented tooth. At this point, the 3-D position for each of the voxels is defined with respect to the CBCT volume coordinate system.

In a reference mark selection step S106 in the sequence of FIG. 2, the CBCT volume images display with two or more different 2-D views, obtained with respect to different view angles. The different 2-D views can be at different angles and may be different image slices, or may be orthographic or substantially orthographic projections, or may be perspective views, for example.

Figure 5:
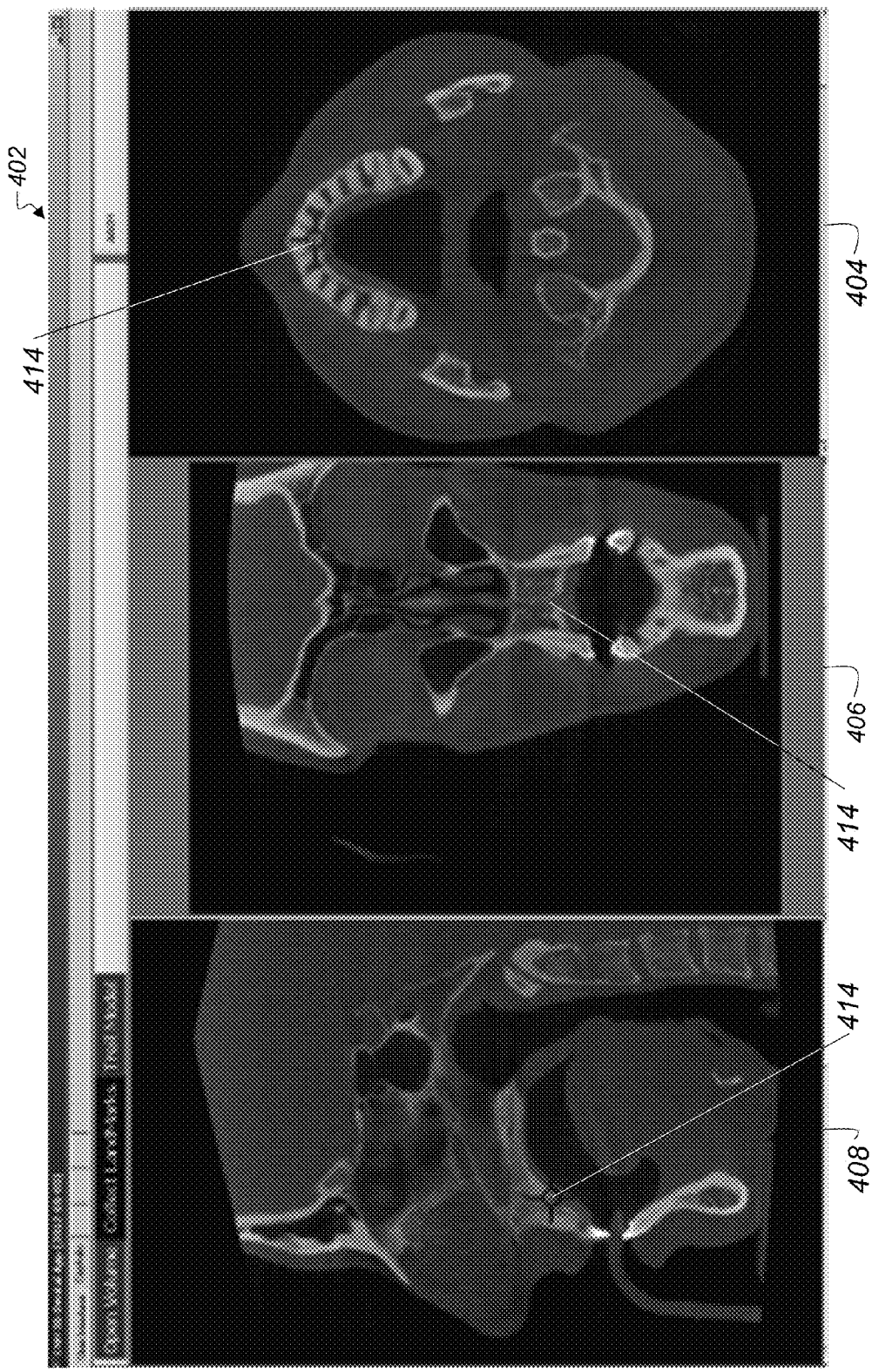
FIG. 5 is a view of a user interface that displays three orthogonal views of the CBCT head volume images that are slices or section views of a volume and operator-entered reference marks.

FIG. 5 shows an exemplary format with a display interface 402 showing three orthogonal 2-D views. In display interface 402, an image 404 is one of the axial 2-D views of the CBCT volume image 202 (FIG. 3), an image 406 is one of the coronal 2-D views of the CBCT volume image 202, and an image 408 is one of the sagittal 2-D views of the CBCT volume image 202. The display interface allows a viewer, such as a practitioner or technician, to interact with the computer system that executes various image processing/computer algorithms in order to accomplish a plurality of 3-D cephalometric analysis tasks. Viewer interaction can take any of a number of forms known to those skilled in the user interface arts, such as using a pointer such as a computer mouse joystick or touchpad, or using a touch screen for selecting an action or specifying a coordinate of the image, for interaction described in more detail subsequently.

Figure 6:
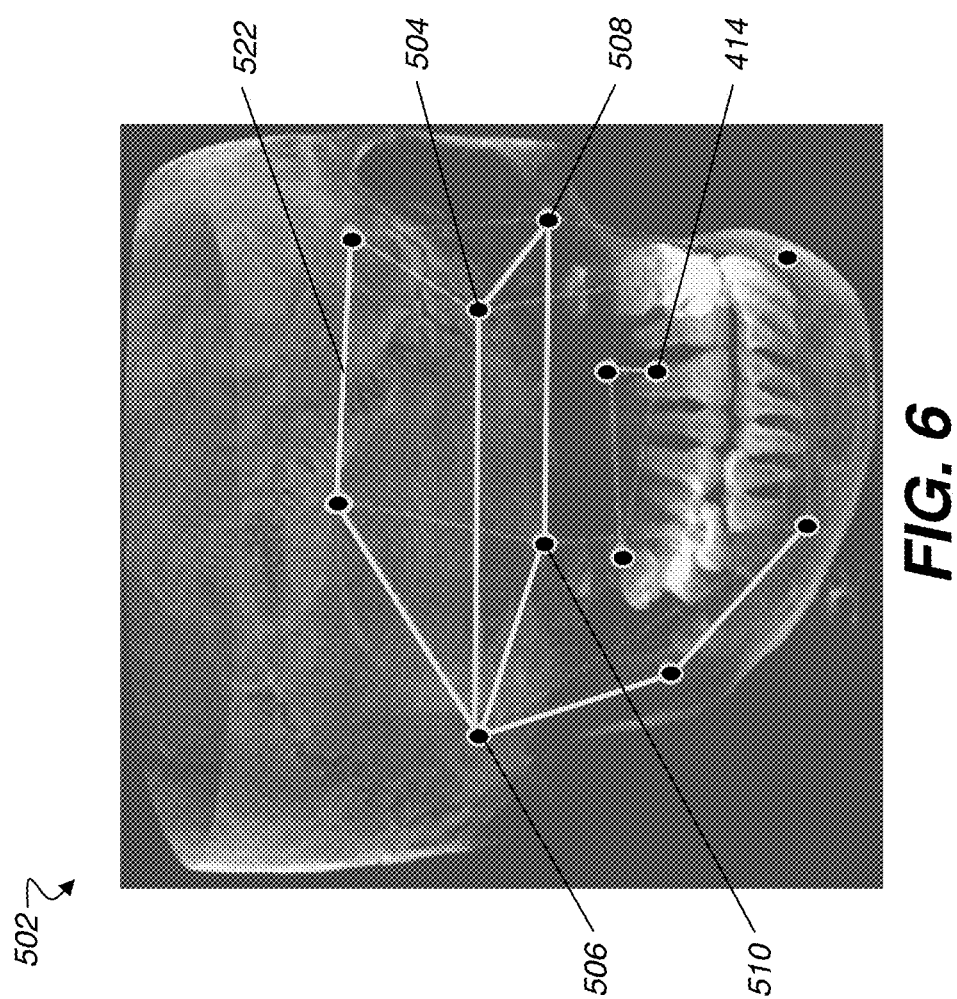
FIG. 6 is a view that is a projection image of a volume from a particular angle of 3-D rendered CBCT head volume images with a set 3-D reference marks displayed.

One of the 3-D cephalometric analysis tasks is to perform automatic identification in 3-D reference mark selection step S106 of FIG. 2. The 3-D reference marks, equivalent to a type of 3-D landmark or feature point identified by the viewer on the displayed image, are shown in the different mutually orthogonal 2-D views of display interface 402 in FIG. 5. Exemplary 3-D anatomic reference marks shown in FIG. 5 are lower nasal palatine foramen at reference mark 414. As shown in FIG. 6, other anatomic reference marks that can be indicated by the viewer on a displayed image 502 include infraorbital foramina at reference marks 508 and 510, and malleus at reference marks 504 and 506.

In step S106, the viewer uses a pointing device (such as a mouse or touch screen, for example) to place a reference mark as a type of geometric primitive at an appropriate position in any one of the three views. According to an embodiment of the present invention that is shown in figures of the present disclosure, the reference mark displays as a circle. Using the display interface screen of FIG. 5, for example, the viewer places a small circle in the view shown as image 404 at location 414 as the reference mark for a reference point.

Reference mark 414 displays as a small circle in image 404 as well as at the proper position in corresponding views in images 406 and 408. It is instructive to note that the viewer need only indicate the location of the reference mark 414 in one of the displayed views 404, 406 or 408; the system responds by showing the same reference mark 414 in other views of the patient anatomy. Thus, the viewer can identify the reference mark 414 in the view in which it is most readily visible.

After entering the reference mark 414, the user can use operator interface tools such as the keyboard or displayed icons in order to adjust the position of the reference mark 414 on any of the displayed views. The viewer also has the option to remove the entered reference mark and enter a new one.

The display interface 402 (FIG. 5) provides zoom in/out utilities for re-sizing any or all of the displayed views. The viewer can thus manipulate the different images efficiently for improved reference mark positioning.

The collection of reference mark entries, made with reference to and appearing on views of the 3-D image content, provides a set of cephalometric parameters that can be used for a more precise characterization of the patient's head shape and structure.

Cephalometric parameters include coordinate information that is provided directly by the reference mark entry for particular features of the patient's head. Cephalometric parameters also include information on various measurable characteristics of the anatomy of a patient's head that are not directly entered as coordinate or geometric structures but are derived from coordinate information, termed "derived cephalometric parameters". Derived cephalometric parameters can provide information on relative size or volume, symmetry, orientation, shape, movement paths and possible range of movement, axes of inertia, center of mass, and other data. In the context of the present disclosure, the term "cephalometric parameters" applies to those that are either directly identified, such as by the reference marks, or those derived cephalometric parameters that are computed according to the reference marks. For example, as particular reference points are identified by their corresponding reference marks, framework connecting lines 522 are constructed to join the reference points for a suitable characterization of overall features, as is more clearly shown in FIG. 6. Framework connecting lines 522 can be considered as vectors in 3-D space; their dimensional and spatial characteristics provide additional volume image data that can be used in computation for orthodontia and other purposes.

Figure 7C:
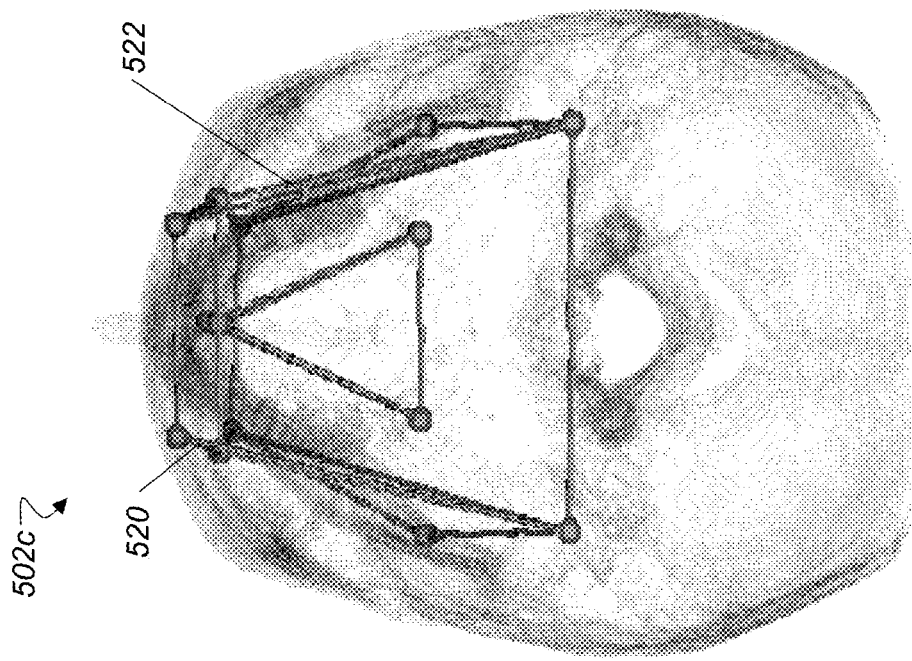
Figure 7B:
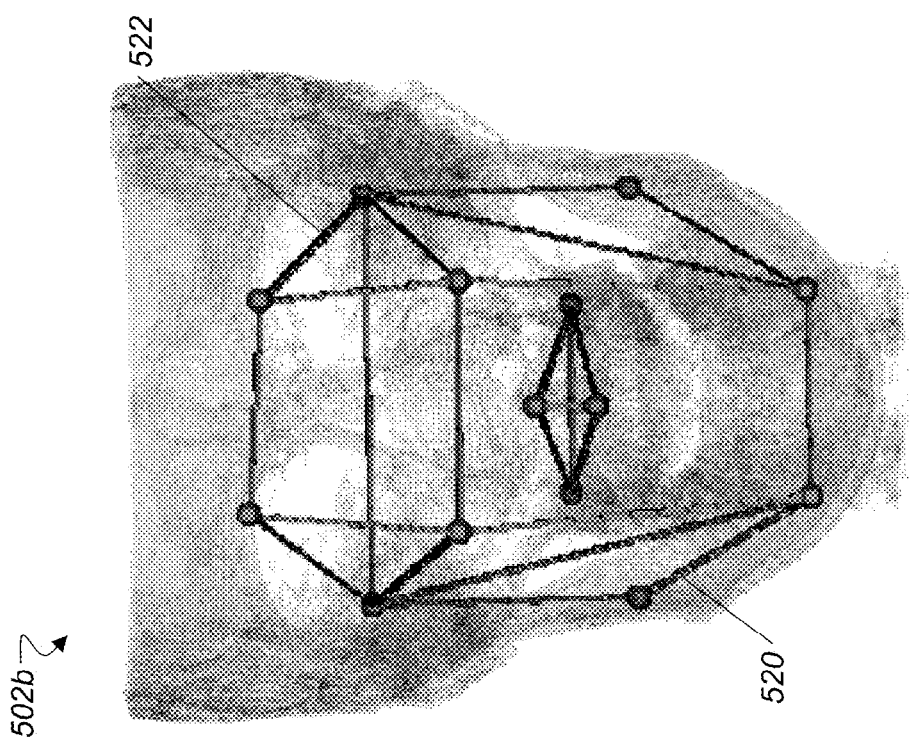

Each reference mark 414, 504, 506, 508, 510 is the terminal point for one or more framework connecting lines 522, generated automatically within the volume data by computer 106 of image processing apparatus 100 and forming a framework that facilitates subsequent analysis and measurement processing. FIGS. 7A, 7B, and 7C show, for displayed images 502a, 502b, and 502c from different perspective views, how a framework 520 of selected reference points, with the reference points at the vertices, helps to define dimensional aspects of the overall head structure. According to an embodiment of the present invention, an operator instruction allows the operator to toggle between 2-D views similar to those shown in FIG. 5 and the volume representation shown in FIG. 6, with partial transparency for voxels of the patient's head. This enables the operator to examine reference mark and connecting line placement from a number of angles; adjustment of reference mark position can be made on any of the displayed views. In addition, according to an embodiment of the present invention, the operator can type in more precise coordinates for a specific reference mark.

The logic flow diagram of FIG. 8 shows steps in a sequence for accepting and processing operator instructions for reference mark entry and identification and for providing computed parameters according to the image data and reference marks. A display step S200 displays one or more 2-D views, from different angles, such as from mutually orthogonal angles, for example, of reconstructed 3-D image data from a computed tomographic scan of a patient's head. In an optional listing step S210, the system provides a text listing such as a tabular list, a series of prompts, or a succession of labeled fields for numeric entry that requires entry of positional data for a number of landmarks or anatomical features in the reconstructed 3-D image. This listing may be explicitly provided for the operator in the form of user interface prompts or menu selection, as described subsequently. Alternately, the listing may be implicitly defined, so that the operator need not follow a specific sequence for entering positional information. Reference marks that give the x, y, z positional data for different anatomical features are entered in a recording step S220. In recording step S220, the system accepts operator instructions that position a reference mark corresponding to each landmark feature of the anatomy. The reference mark is entered by the operator on either the first or the second 2-D view, or on any of the other views if more than two views are presented and, following entry, displays on each of the displayed views. An identification step S230 identifies the anatomical feature or landmark that corresponds to the entered reference mark and, optionally, verifies the accuracy of the operator entry. Proportional values are calculated to determine the likelihood that a given operator entry accurately identifies the position of a reference mark for a particular anatomical feature. For example, the infraorbital foramen is typically within a certain distance range from the palatine foramen; the system checks the entered distance and notifies the operator if the corresponding reference mark does not appear to be properly positioned.

Continuing with the sequence of FIG. 8, in a construction step S240, framework connecting lines are generated to connect reference marks for frame generation. A computation and display step S250 is then executed, computing one or more cephalometric parameters according to the positioned reference marks. The computed parameters are then displayed to the operator.

Figure 9B:
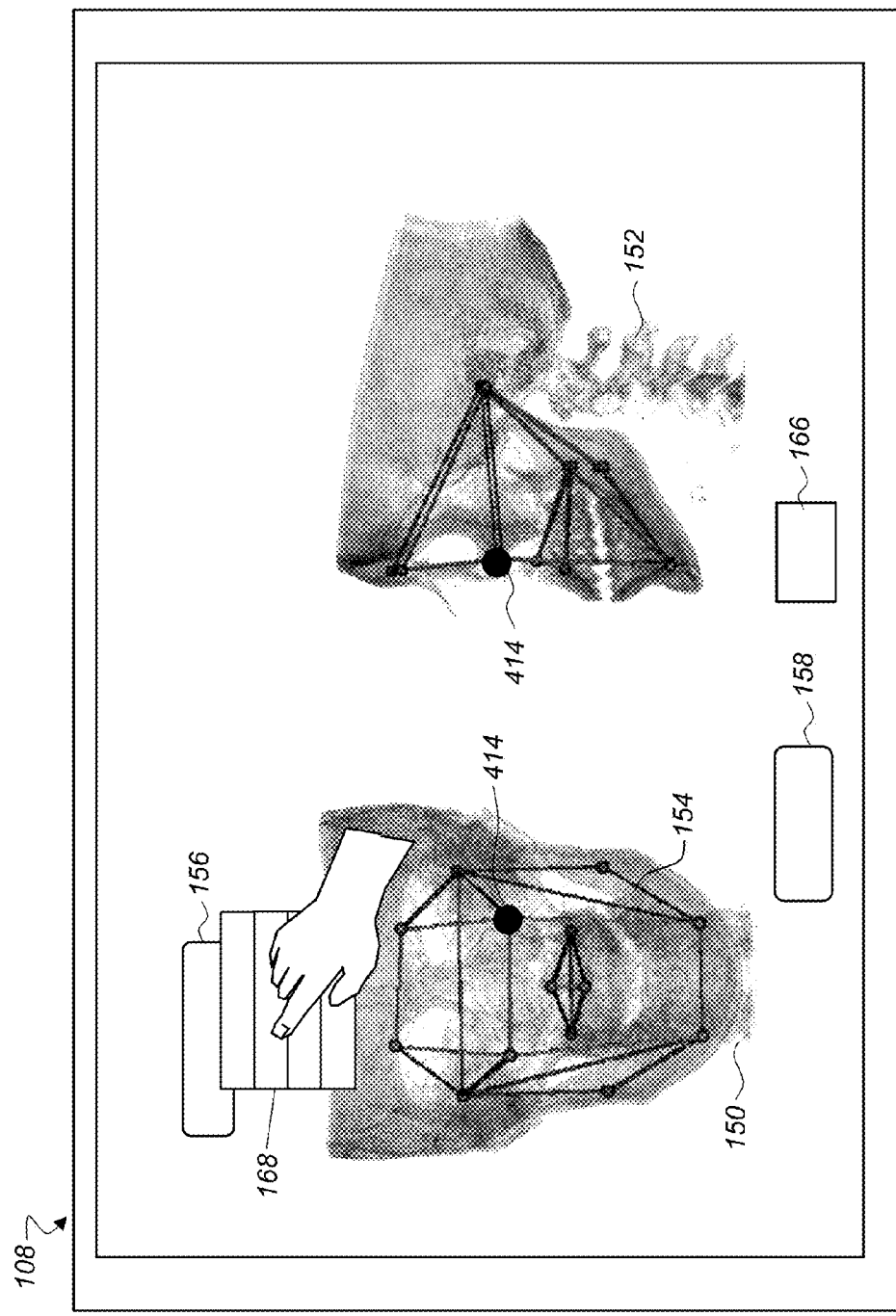

FIGS. 9A, 9B, and 9C show an operator interface appearing on display 108. The operator interface provides, on display 108, an interactive utility for accepting operator instructions and for displaying computation results for cephalometric parameters of a particular patient. Display 108 can be a touch screen display for entry of operator-specified reference marks and other instructions, for example. Display 108 simultaneously displays at least one 2-D view of the volume image data or two or more 2-D views of the volume image data from different angles or perspectives. By way of example, FIG. 9A shows a frontal or coronal view 150 paired with a side or sagittal view 152. More than two views can be shown simultaneously and different 2-D views can be shown, with each of the displayed views independently positioned according to an embodiment of the present invention. Views can be mutually orthogonal or may simply be from different angles. As part of the interface of display 108, an optional control 166 enables the viewer to adjust the perspective angle from which one or more of the 2-D views are obtained, either by toggling between alternate fixed views or by changing the relative perspective angle in increments along any of the 3-D axes (x, y, z). A corresponding control 166 can be provided with each 2-D view, as shown in FIG. 9-C.

Using the operator interface shown for display 108, each reference mark 414 is entered by the operator using a pointer of some type, which may be a mouse or other electronic pointer or may be a touchscreen entry as shown in FIG. 9A. As part of the operator interface, an optional listing 156 is provided to either guide the operator to enter a specific reference mark according to a prompt, or to identify the operator entry, such as by selection from a drop-down menu 168 as shown in the example of FIG. 9B. Thus, the operator can enter a value in listing 156 or may enter a value in field 158, then select the name associated with the entered value from drop-down menu 168. FIGS. 9A-9C show a framework 154 constructed between reference points. As FIG. 9A shows, each entered reference mark 414 may be shown in both views 150 and 152. A selected reference mark 414 is highlighted on display 108, such as appearing in bold or in another color. A particular reference mark is selected in order to obtain or enter information about the reference mark or to perform some action, such as to shift its position, for example.

In the embodiment shown in FIG. 9B, the reference mark 414 just entered or selected by the operator is identified by selection from a listing 156. For the example shown, the operator selects the indicated reference mark 414, then makes a menu selection such as "infraorbital foramen" from menu 168. An optional field 158 identifies the highlighted reference mark 414. Calculations based on a model or based on standard known anatomical relationships can be used to identify reference mark 414, for example.

FIG. 9C shows an example in which the operator enters a reference mark 414 instruction that is detected by the system as incorrect or unlikely. An error prompt or error message 160 displays, indicating that the operator entry appears to be in error. The system computes a probable location for a particular landmark or anatomical feature based on a model or based on learned data, for example. When the operator entry appears to be inaccurate, message 160 displays, along with an optional alternate location 416. An override instruction 162 displays, along with a repositioning instruction 164 for repositioning the reference mark according to the calculated information from the system. Repositioning can be done by accepting another operator entry from the display screen or keyboard or by accepting the system-computed reference mark location, at alternate location 416 in the example of FIG. 9C.

According to an alternate embodiment of the present invention, the operator does not need to label reference marks as they are entered. Instead the display prompts the operator to indicate a specific landmark or anatomical feature on any of the displayed 2-D views and automatically labels the indicated feature. In this guided sequence, the operator responds to each system prompt by indicating the position of the corresponding reference mark for the specified landmark.

According to another alternate embodiment of the present invention, the system determines which landmark or anatomical feature has been identified as the operator indicates a reference mark; the operator does not need to label reference marks as they are entered. The system computes the most likely reference mark using known information about anatomical features that have already been identified and, alternately, by computation using the dimensions of the reconstructed 3-D image itself.

Using the operator interface shown in the examples of FIGS. 9A-9C, embodiments of the present invention provide a practical 3-D cephalometric analysis system that synergistically integrates the skills of the human operator of the system with the power of the computer in the process of 3-D cephalometric analysis. This takes advantage of human skills of creativity, use of heuristics, flexibility, and judgment, and combines these with computer advantages, such as speed of computation, capability for accurate and repeatable processing, reporting and data access and storage capabilities, and display flexibility.

Referring back to the sequence of FIG. 2, derived cephalometric parameters are computed in a computation step S108 once a sufficient set of landmarks is entered. FIGS. 10A through 10E show a processing sequence for computing and analyzing cephalometric data and shows how a number of cephalometric parameters are obtained from combined volume image data and anatomical features information according to operator entered instructions. According to an embodiment of the present invention, portions of the features shown in FIGS. 10A through 10E are displayed on display 108 (FIG. 1).

Figure 10A:
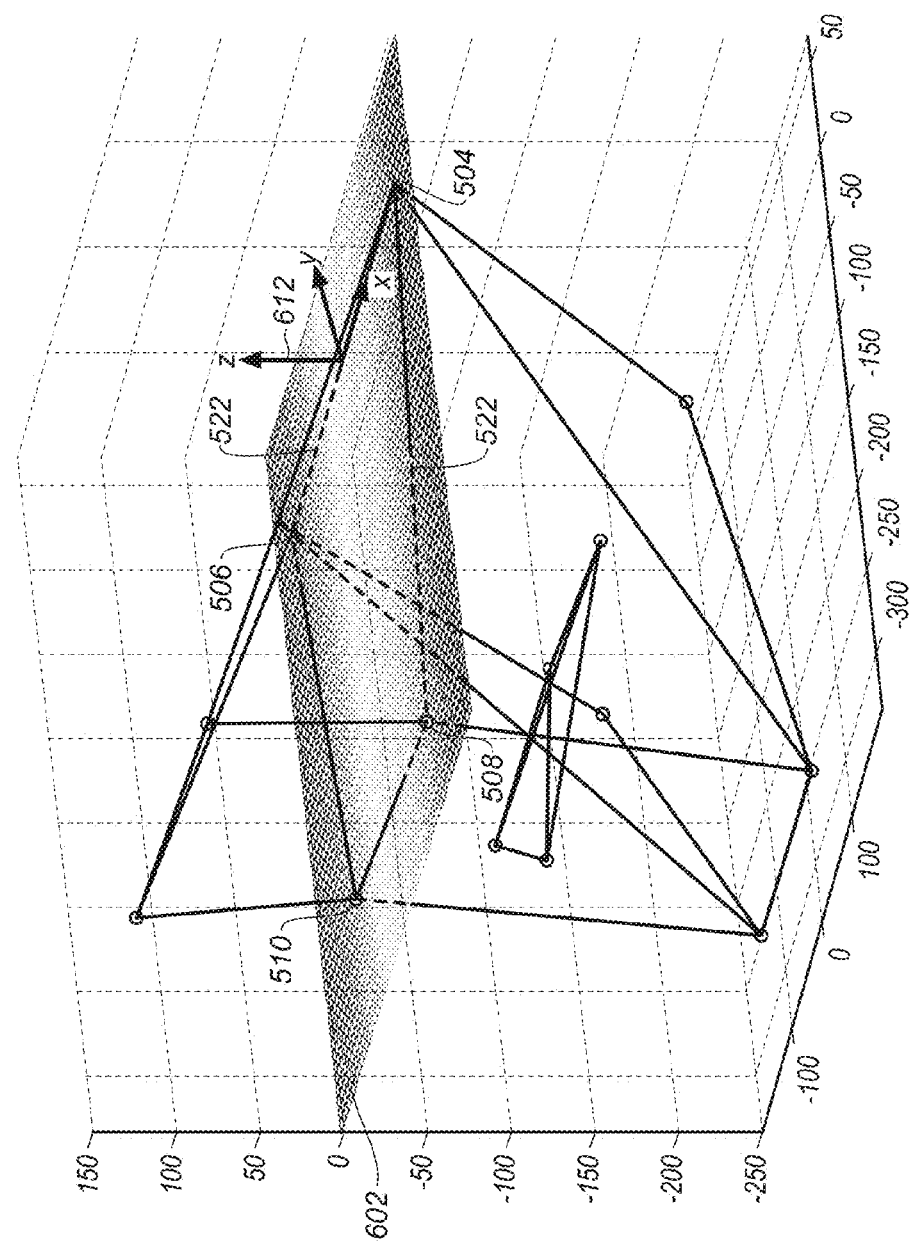
FIGS. 10A, 10B, 10C, 10D, and 10E are graphs that show how various derived parameters are calculated using the volume image data and corresponding operator-entered reference marks.

An exemplary derived cephalometric parameter shown in FIG. 10A is a 3-D plane 602 (termed a t-reference plane in cephalometric analysis) that is computed by using a subset of the set of first geometric primitives with reference marks 504, 506, 508 and 510 as previously described with reference to FIG. 6. A further derived cephalometric parameter is 3-D coordinate reference system 612 termed a t-reference system and described by Treil in publications noted previously. The z axis of the t-reference system 612 is chosen as perpendicular to the 3-D t-reference plane 602. The y axis of the t-reference system 612 is aligned with framework connecting line 522 between reference marks 508 and 504. The x axis of the t-reference system 612 is in plane 602 and is orthogonal to both z and x axes of the t-reference system. The directions of t-reference system axes are indicated in FIG. 10A and in subsequent FIGS. 10B, 10C, 10D, and 10E. The origin of the t-reference system is at the middle of framework connecting line 522 that connects reference marks 504 and 506. With the establishment of t-reference system 612, 3-D reference marks from step S106 and 3-D teeth data (3-D position list of a tooth) from step S104 are transformed from the CBCT volume coordinate system to t-reference system 612. With this transformation, subsequent computations of derived cephalometric parameters and analyses can now be performed with respect to t-reference system 612.

Figure 10B:
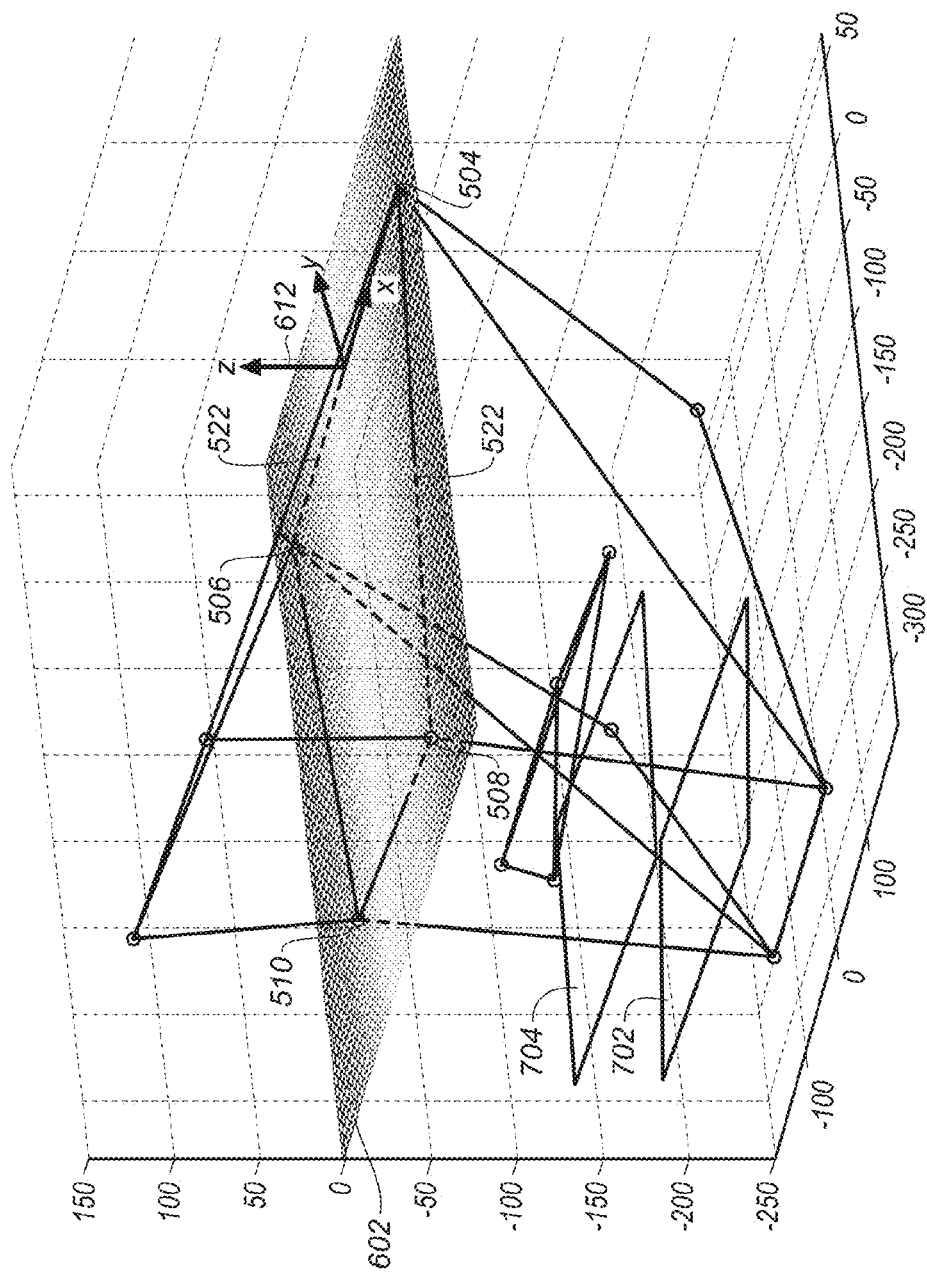

Referring to FIG. 10B, a 3-D upper jaw plane 704 and a 3-D lower jaw plane 702 can be derived from cephalometric parameters from the teeth data in t-reference system 612. The derived upper jaw plane 704 is computed according to teeth data segmented from the upper jaw (maxilla). Using methods familiar to those skilled in cephalometric measurement and analysis, derived lower jaw plane 702 is similarly computed according to the teeth data segmented from the lower jaw (mandibular).

For an exemplary computation of a 3-D plane from the teeth data, an inertia tensor is formed by using the 3-D position vectors and code values of voxels of all teeth in a jaw (as described in the cited publications by Treil); eigenvectors are then computed from the inertia tensor. These eigenvectors mathematically describe the orientation of the jaw in the t-reference system 612. A 3-D plane can be formed using two of the eigenvectors, or using one of the eigenvectors as the plane normal.

Figure 10C:
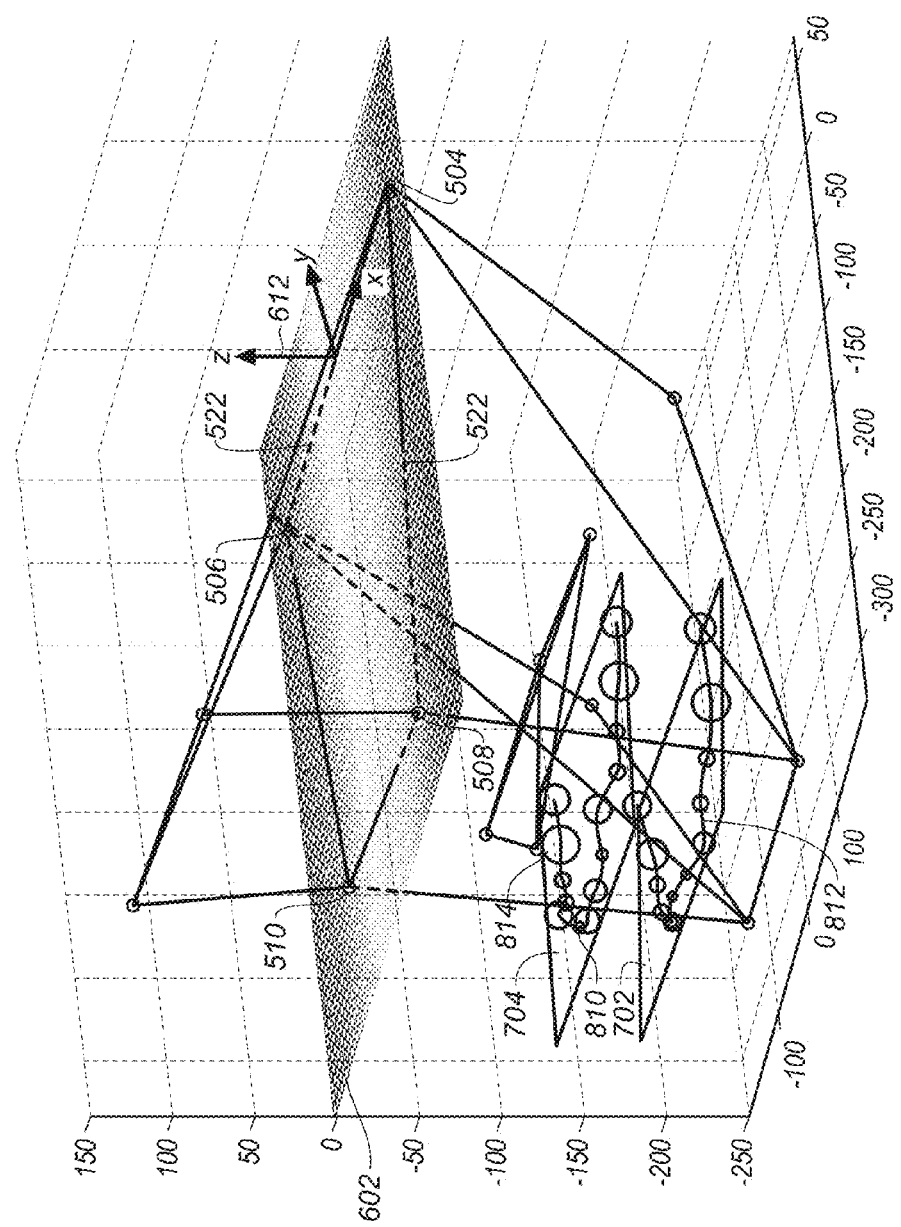

Referring to FIG. 10C, further derived parameters are shown. For each jaw, jaw curves are computed as derived parameters. An upper jaw curve 810 is computed for the upper jaw; a lower jaw curve 812 is derived for the lower jaw. The jaw curve is constructed to intersect with the mass center of each tooth in the respective jaw and to lie in the corresponding jaw plane. The mass center of the tooth can be calculated, in turn, using the 3-D position list and the code value list for the segmented teeth.

The mass of a tooth is also a derived cephalometric parameter computed from the code value list of a tooth. In FIG. 10C, an exemplary tooth mass is displayed as a circle 814 or other type of shape for an upper jaw tooth.

According to an embodiment of the present invention, one or more of the relative dimensions of the shape, such as the circle radius, for example, indicates relative mass value, the mass value of the particular tooth in relation to the mass of other teeth in the jaw. For example, the first molar of the upper jaw has a mass value larger than the neighboring teeth mass values.

According to an embodiment of the present invention, for each tooth, an eigenvector system is also computed. An inertia tensor is initially formed by using the 3-D position vectors and code values of voxels of a tooth, as described in the cited publications by Treil. Eigenvectors are then computed as derived cephalometric parameters from the inertia tensor. These eigenvectors mathematically describe the orientation of a tooth in the t-reference system.

Figure 10D:
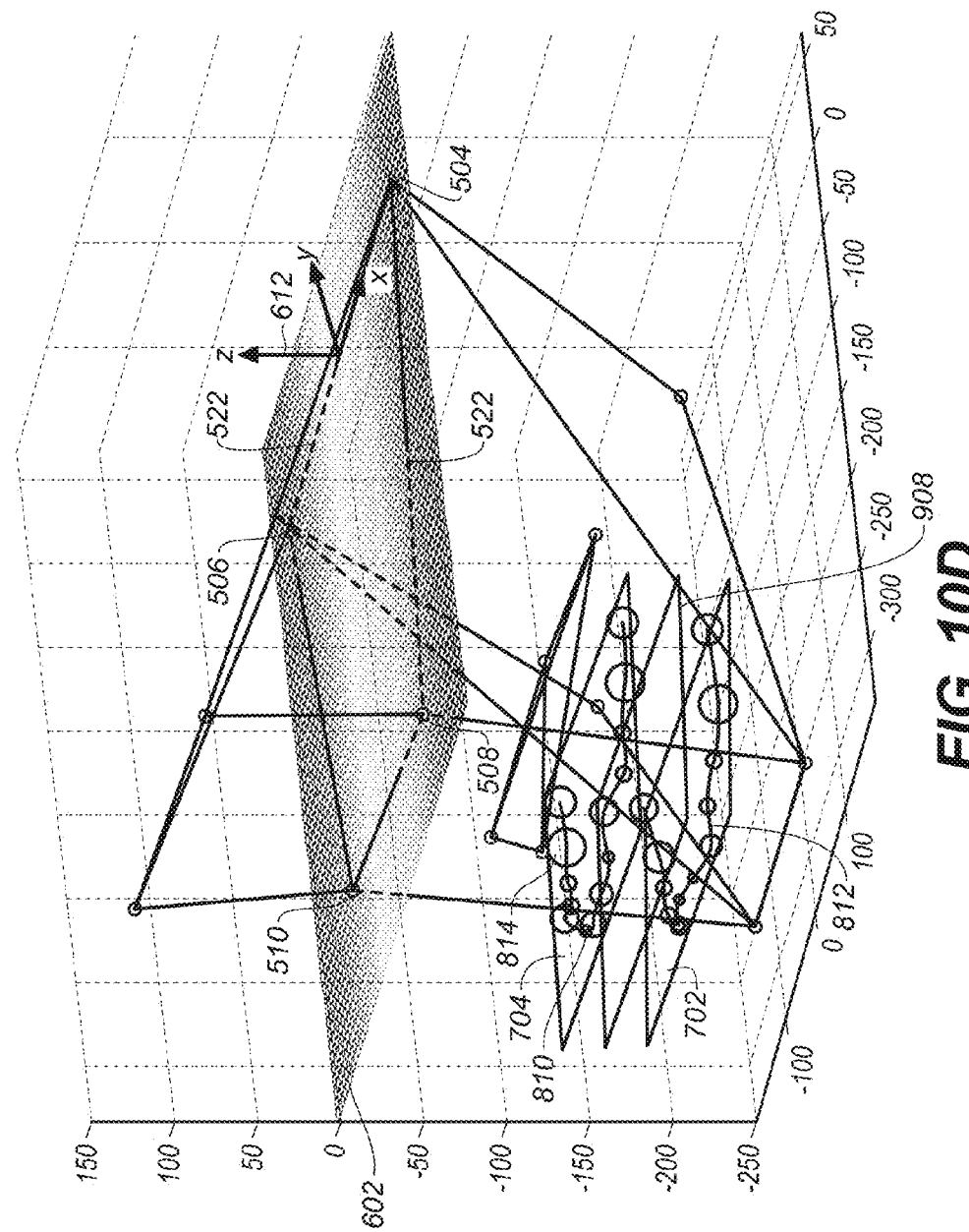

As shown in FIG. 10D, another derived parameter, an occlusal plane, 3-D plane 908, is computed from the two jaw planes 702 and 704. Occlusal plane, 3-D plane 908, lies between the two jaw planes 702 and 704. The normal of plane 908 is the average of the normal of plane 702 and normal of plane 704.

Figure 10E:
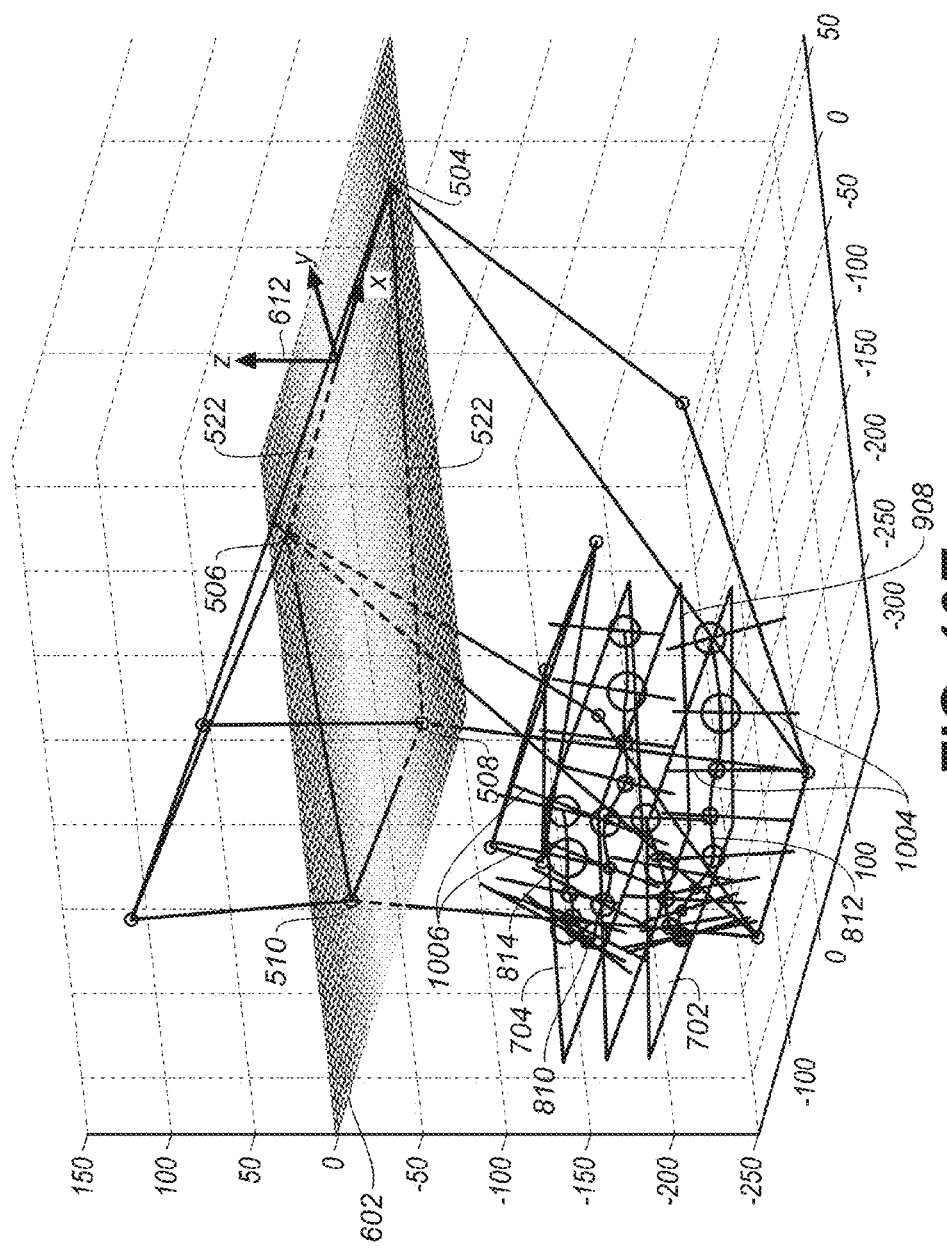

For an individual tooth, in general, the eigenvector corresponding to the largest computed eigenvalue is another derived cephalometric parameter that indicates the medial axis of the tooth. FIG. 10E shows two types of exemplary medial axes for teeth: medial axes 1006 for upper incisors and medial axes 1004 for lower incisors.

The calculated length of the medial axis of a tooth is a useful cephalometric parameter in cephalometric analysis and treatment planning along with other derived parameters. It should be noted that, instead of using the eigenvalue to set the length of the axis as proposed in the cited publication by Treil, embodiments of the present invention compute the actual medial axis length as a derived parameter using a different approach. A first intersection point of the medial axis with the bottom slice of the tooth volume is initially located. Then, a second intersection point of the medial axis with the top slice of the tooth volume is identified. An embodiment of the present invention then computes the length between the two intersection points.

Figure 11:
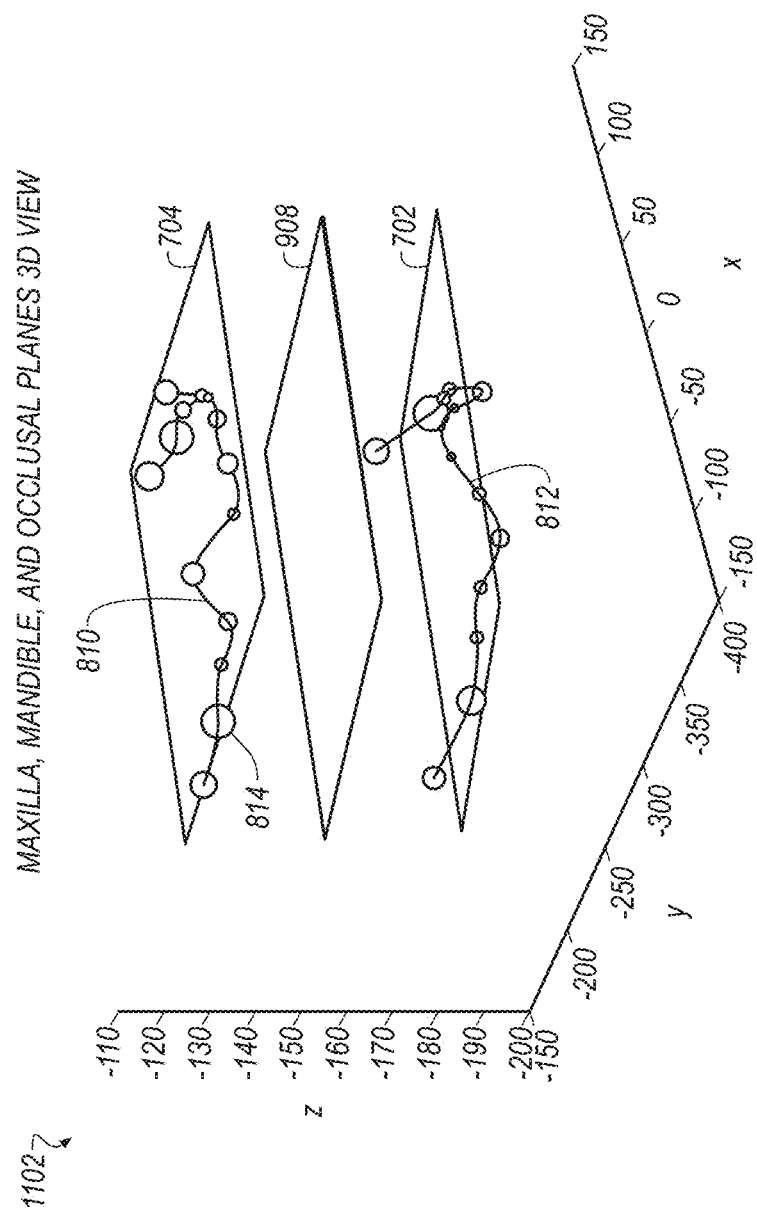
FIG. 11 is a 3-D graph showing a number of derived cephalometric parameters from segmented teeth data.

FIG. 11 shows a graph 1102 that provides a closeup view that isolates the occlusal plane 908 in relation to upper jaw plane 704 and lower jaw plane 702 and shows the relative positions and curvature of jaw curves 810 and 812.

Figure 12:
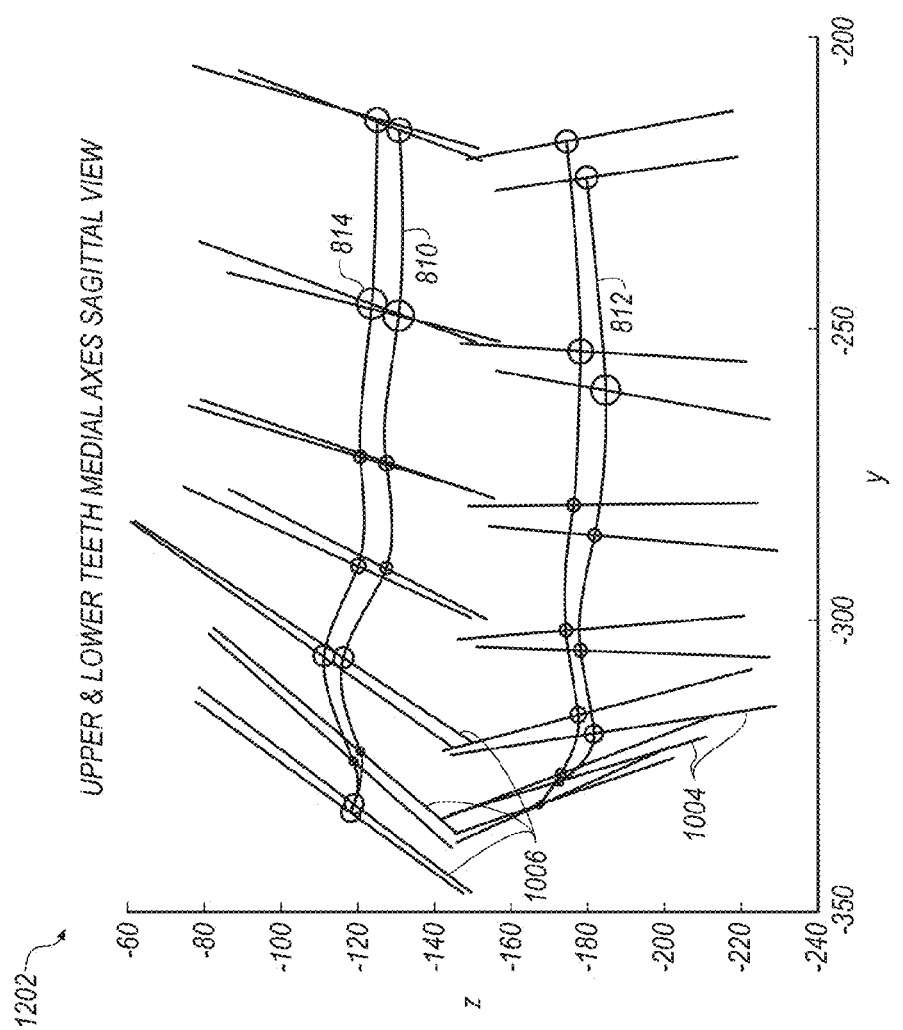
FIG. 12 is a 2-D graph showing the derived cephalometric parameters from segmented teeth data.

FIG. 12 shows a graph 1202 that shows the positional and angular relationships between the upper teeth medial axes 1006 and the lower teeth medial axes 1004.

As noted in the preceding descriptions and shown in the corresponding figures, there are a number of cephalometric parameters that can be derived from the combined volume image data and operator-entered reference marks. These are computed in a cephalometric analysis step S110 (FIG. 2).

One exemplary 3-D cephalometric analysis procedure in step S110 that can be particularly valuable relates to the relative parallelism of the maxilla (upper jaw) and mandibular (lower jaw) planes 702 and 704. Both upper and lower jaw planes 702 and 704, respectively, are derived parameters, as noted previously. The assessment can be done using the following sequence:

Project the x axis of the maxilla inertia system (that is, the eigenvectors) to the x-z plane of the t-reference system and compute an angle MX1_RF between the z axis of the t-reference system and the projection;

Project the x axis of the mandibular inertia system (that is, the eigenvectors) to the x-z plane of the t-reference system and compute an angle MD1_RF between the z axis of the t-reference system and the projection;

MX1_MD1_RF=MX1_RF−MD1_RF gives a parallelism assessment of upper and lower jaws in the x-z plane of the t-reference system;

Project the y axis of the maxilla inertia system (that is, the eigenvectors) to the y-z plane of the t-reference system and compute the angle MX2_RS between the y axis of the t-reference system and the projection;

Project the y axis of the mandibular inertia system (that is, the eigenvectors) to the y-z plane of the t-reference system and compute an angle MD2_RS between the y axis of the t-reference system and the projection;

MX2_MD2_RS=MX2_RS−MD2_RS gives a parallelism assessment of upper and lower jaws in the y-z plane of the t-reference system.

Another exemplary 3-D cephalometric analysis procedure that is executed in step S110 is assessing the angular property between the maxilla (upper jaw) incisor and mandible (lower jaw) incisor using medial axes 1006 and 1004 (FIGS. 10E, 12). The assessment can be done using the following sequence:

Project the upper incisor medial axis 1006 to the x-z plane of the t-reference system and compute an angle MX1_AF between the z axis of the t-reference system and the projection;

Project the lower incisor medial axis 1004 to the x-z plane of the t-reference system and compute an angle MD1_AF between the z axis of the t-reference system and the projection;

MX1_MD1_AF=MX1_AF−MD1_AF gives the angular property assessment of the upper and lower incisors in the x-z plane of the t-reference system;

Project the upper incisor medial axis 1006 to the y-z plane of the t-reference system and compute an angle MX2_AS between the y axis of the t-reference system and the projection;

Project the lower incisor medial axis 1004 to the y-z plane of the t-reference system and compute an angle MD2_AS between the y axis of the t-reference system and the projection;

MX2_MD2_AS=MX2_AS−MD2_AS gives the angular property assessment of upper and lower incisors in the y-z plane of the t-reference system.

Figure 13:
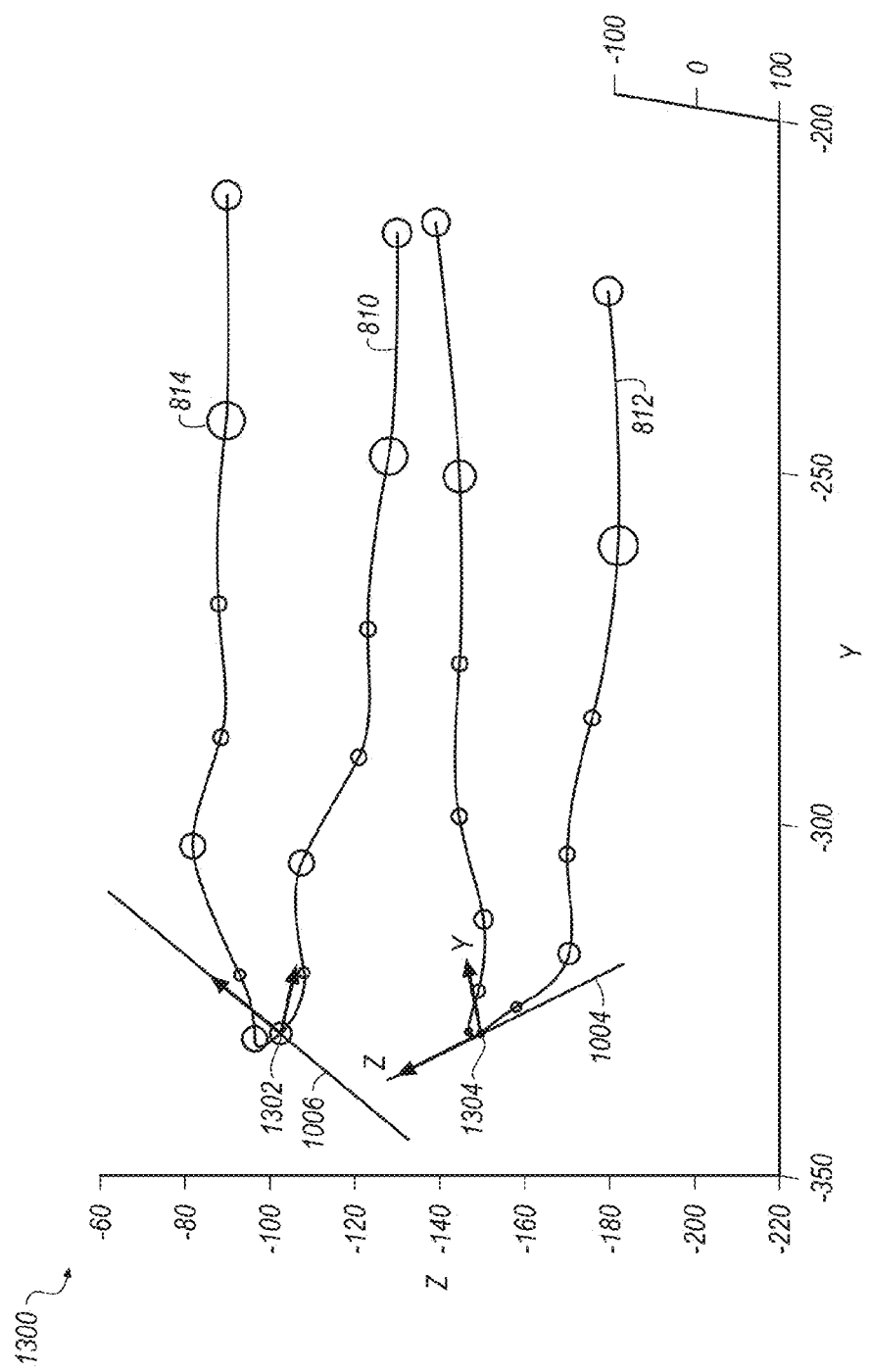
FIG. 13 is another 3-D graph showing the derived cephalometric parameters from segmented teeth data.

FIG. 13 shows a graph 1300 that shows a local x-y-z coordinate system 1302 for an upper incisor, and a local x-y-z coordinate system 1304 for a lower incisor. The local axes of the x-y-z coordinate system align with the eigenvectors associated with that particular tooth. The x axis is not shown but satisfies the right-hand system rule.

In FIG. 13, the origin of system 1302 can be selected at any place along axis 1006. An exemplary origin for system 1302 is the mass center of the tooth that is associated with axis 1006. Similarly, the origin of system 1304 can be selected at any place along axis 1004. An exemplary origin for system 1304 is the mass center of the tooth that is associated with axis 1004.

Figure 14:
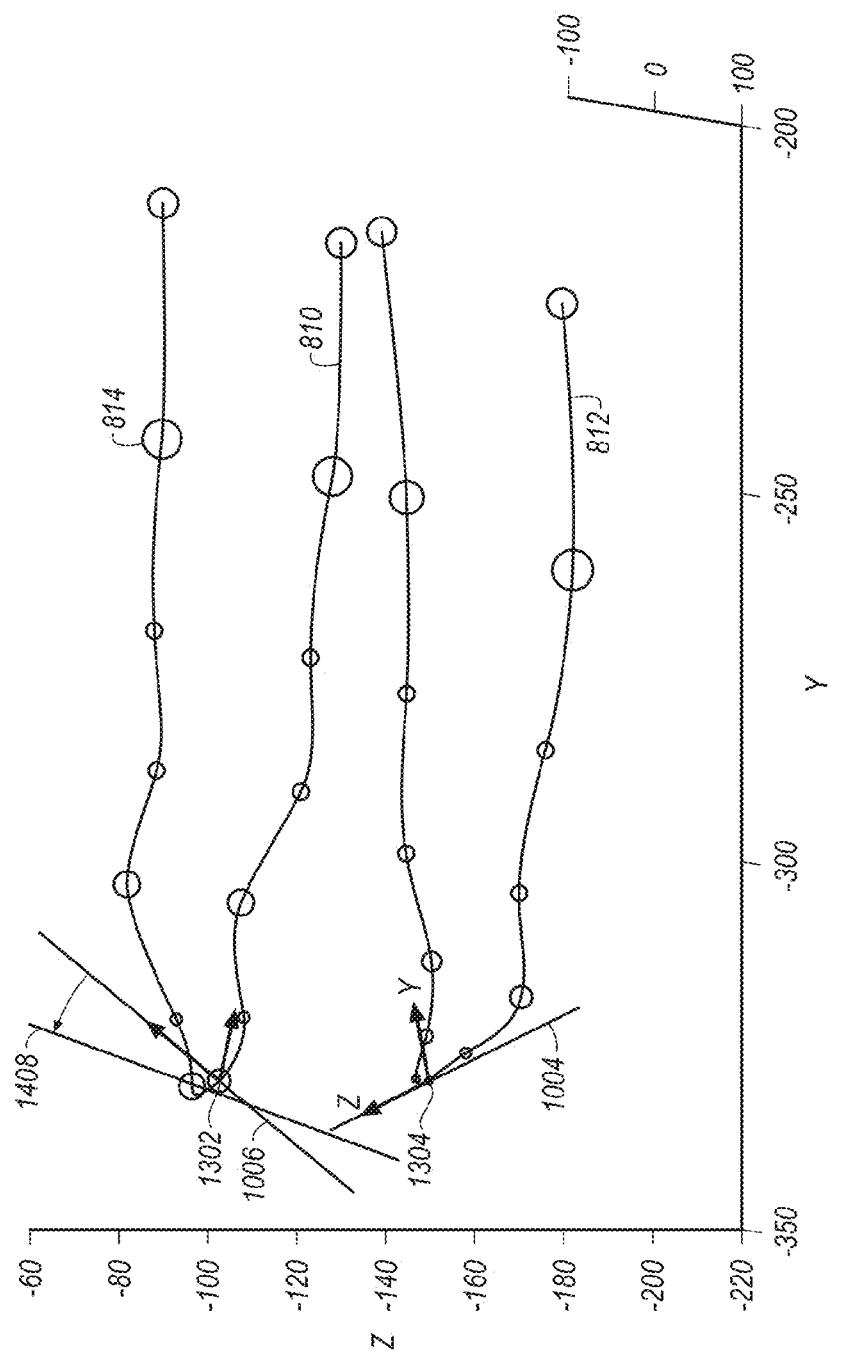
FIG. 14 is a graph showing the derived cephalometric parameters from segmented teeth data and treatment parameter.

Based on the analysis performed in Step S110 (FIG. 2), an adjustment or treatment plan is arranged in a planning step S112. An exemplary treatment plan is to rotate the upper incisor counter clockwise at a 3-D point, such as at its local coordinate system origin, and about an arbitrary 3-D axis, such as about the x axis of the local x-y-z system. The graph of FIG. 14 shows rotation to an axis position 1408.

In a treatment step S114 of FIG. 2, treatment is performed based on the planning, for example, based on upper incisor rotation. The treatment planning can be tested and verified visually in a visualization step S116 before the actual treatment takes place.

Referring back to FIG. 2, there is shown a line 120 from Step S114 to Step S102. This indicates that there is a feedback loop in the sequence 200 workflow. After the patient undergoes treatment, either an immediate or a scheduled evaluation of the treatment can be performed by input of relevant data to the system. This relevant data can include results from optical, radiographic, MRI, or ultrasound imaging and/or any meaningful related measurements or results.

Figure 15:
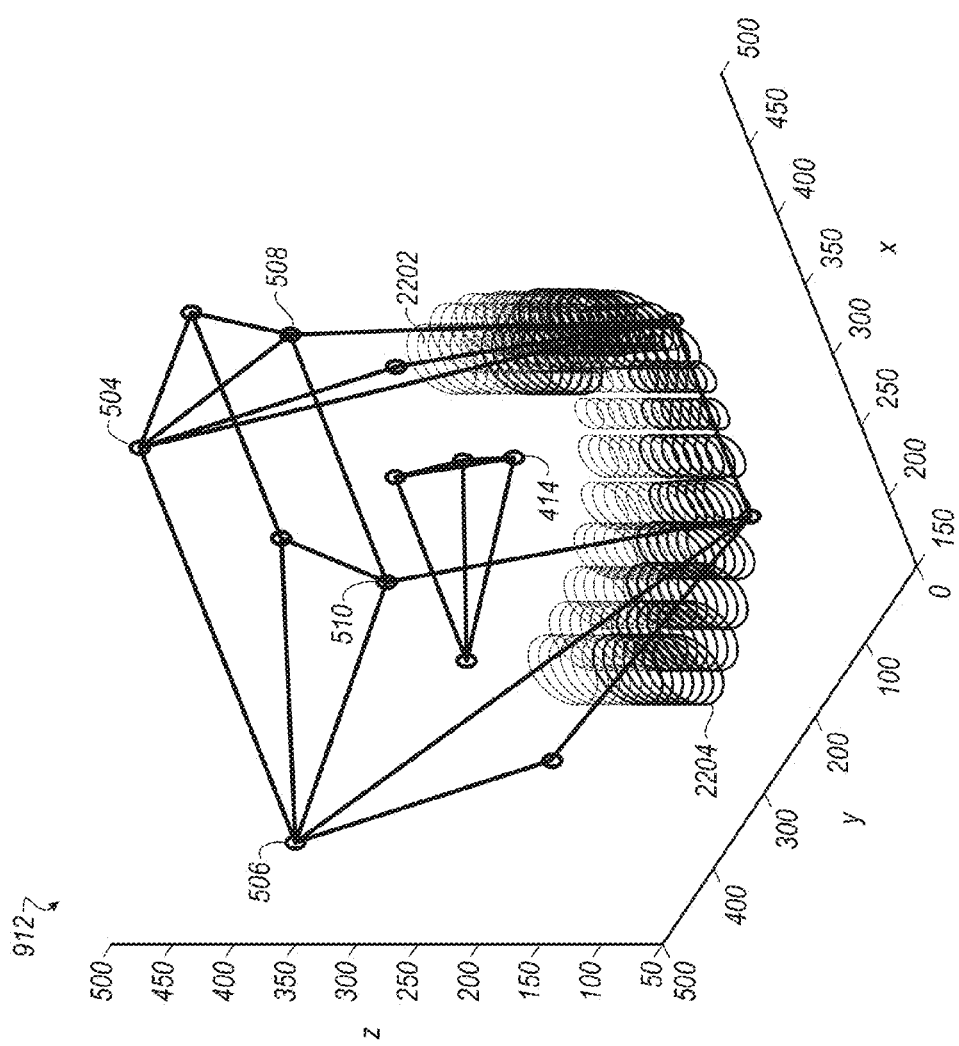
FIG. 15 is a 3-D graph that shows how tooth exclusion is learned by the system.

An optional tooth exclusion step S124 is also shown in sequence 200 of FIG. 2. For this step, the operator specifies one or more teeth, if any, to be excluded from the rest of the processing steps based on Treil's theory of jaw planes parallelism. The graph of FIG. 15 shows how tooth exclusion can be learned by the system, using a virtual or digital phantom 912. Digital phantom 912 is a virtual model used for computation and display that is constructed using a set of landmarks and a set of upper teeth of a digital model of an upper jaw and a set of lower teeth of a digital model of a lower jaw. Digital phantom 912 is a 3-D or volume image data model that is representative of image data that is obtained from patient anatomy and is generated using the landmark and other anatomical information provided and can be stored for reference or may be generated for use as needed. The use of various types of digital phantom is well known to those skilled in the digital radiography arts. The landmarks such as reference marks 504, 506, 508 and 510 of the digital phantom 912 correspond to the actual reference marks identified from the CBCT volume 202 (FIG. 3). These landmarks are used to compute the t-reference system 612 (FIGS. 10A-10E).

The operator can exclude one or more teeth by selecting the teeth from a display or by entering information that identifies the excluded teeth on the display.

In FIG. 15, the upper and lower teeth, such as digital teeth 2202 and 2204 of digital phantom 912 are digitally generated. The exemplary shape of a digital tooth is a cylinder, as shown. The exemplary voxel value for a digital tooth in this example is 255. It can be appreciated that other shapes and values can be used for phantom 912 representation and processing.

Figure 16B:
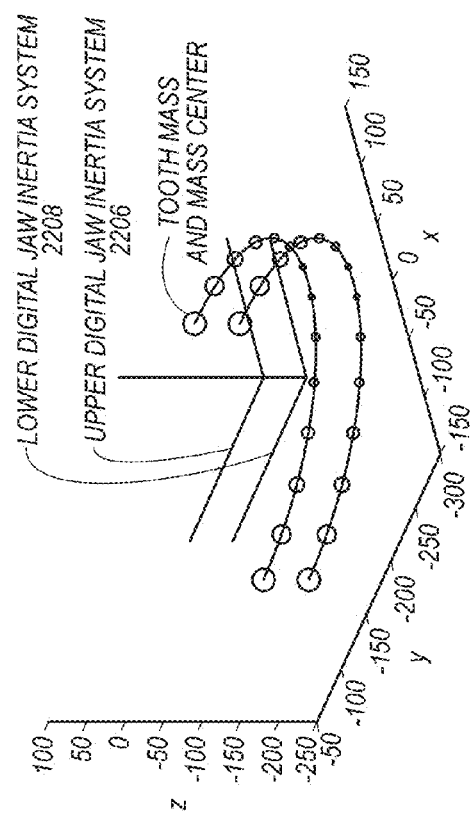
FIG. 16B is a 3-D graph showing computed axes of inertia systems for upper and lower jaws.
Figure 16A:
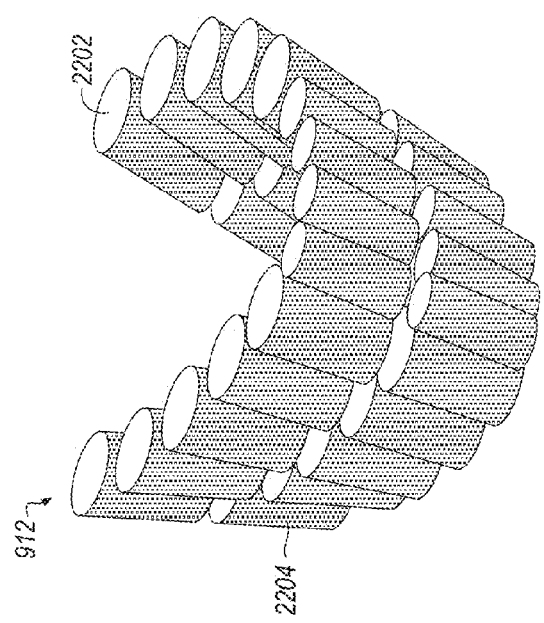
FIG. 16A is a perspective view that shows teeth of a digital phantom.

FIG. 16A shows digital teeth 2202 and 2204 of digital phantom 912. The corresponding digital teeth in the upper digital jaw and lower digital jaw are generated in a same way, with the same size and same code value.

To assess parallelism of the upper and lower digital jaws, an inertia tensor for each digital jaw is formed by using the 3-D position vectors and code values of voxels of all digital teeth in a digital jaw (see the Treil publications, cited previously). Eigenvectors are then computed from the inertia tensor. These eigenvectors, as an inertial system, mathematically describe the orientation of the jaw in the t-reference system 612 (FIG. 10A). As noted earlier, the eigenvectors, computed from the inertial tensor data, are one type of derived cephalometric parameter.

As shown in FIG. 16B, the computed axes of an upper digital jaw inertia system 2206 and a lower digital jaw inertia system 2208 are in parallel for the generated digital phantom 912 as expected, since the upper and lower jaw teeth are created in the same way. FIG. 17A shows this parallelism in the sagittal view along a line 2210 for the upper jaw and along a line 2212 for the lower jaw; FIG. 17B shows parallelism in the frontal (coronal) view at a line 2214 for the upper jaw and at a line 2216 for the lower jaw.

Figure 18B:
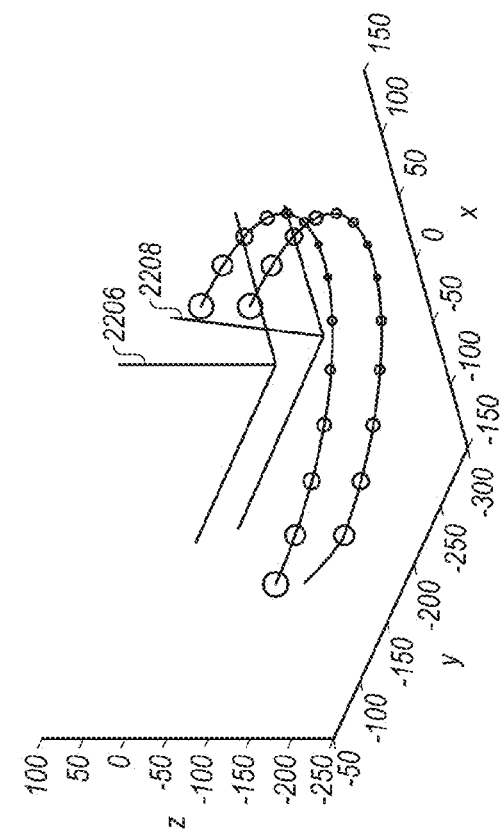
FIG. 18B is a graph showing computed axes of inertia systems for upper and lower jaws for the example of FIG. 18A.
Figure 18A:
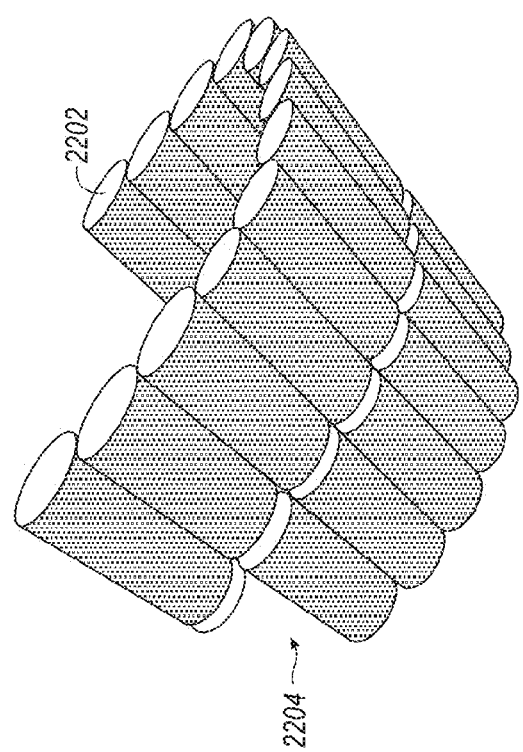
FIG. 18A is a perspective view that shows teeth of a digital phantom with a tooth missing.
Figure 19B:
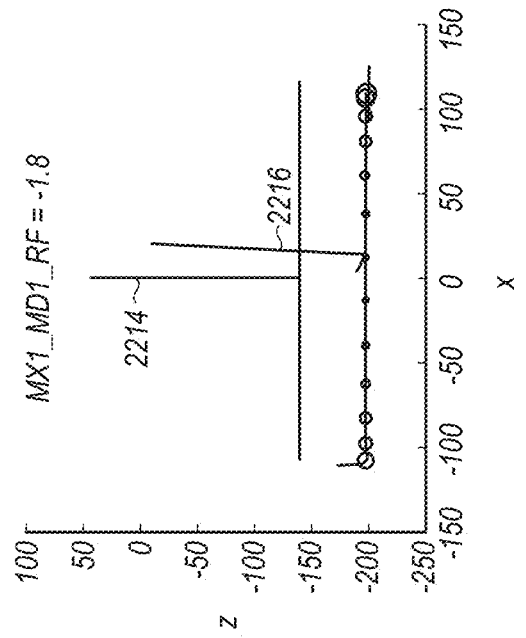
FIG. 19B is a graph showing lack of parallelism for specific tooth structures.
Figure 19A:
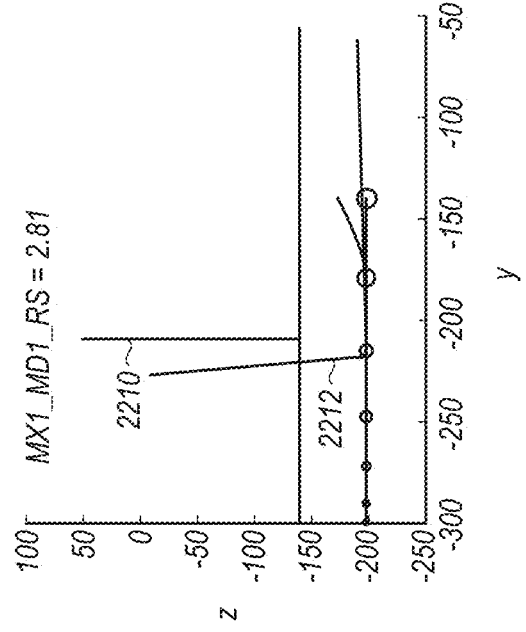
FIG. 19A is a graph showing lack of parallelism for specific tooth structures.
Figure 20B:
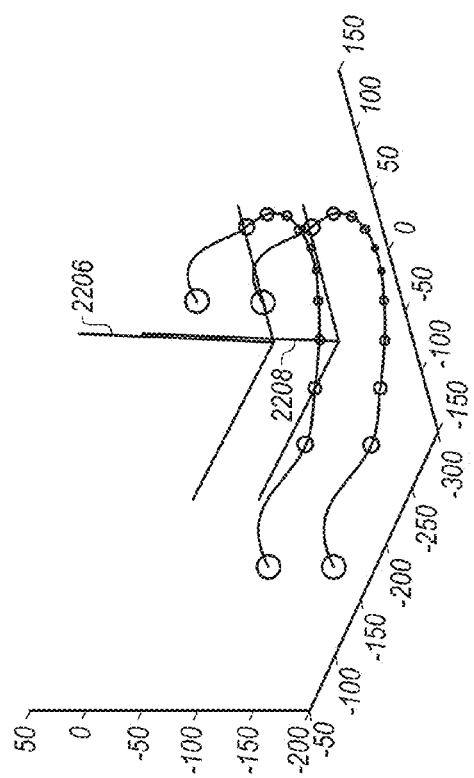
FIG. 20B is a graph showing computed axes of inertia systems for upper and lower jaws for the example of FIG. 20A.
Figure 20A:
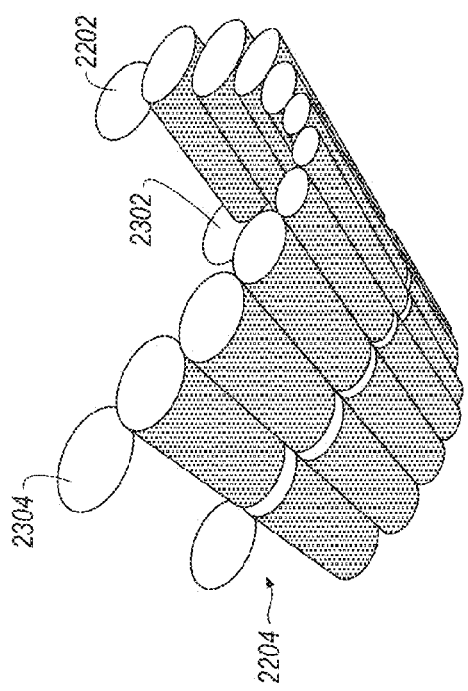
FIG. 20A is a perspective view that shows teeth of a digital phantom with tooth exclusion.

Referring to FIGS. 18A and 18B, there is shown a case in which digital tooth 2204 is missing. The computed axes of upper digital jaw inertia system 2206 and lower digital jaw inertia system 2208 are no longer in parallel. In corresponding FIGS. 19A and 19B, this misalignment can also be examined in a sagittal view along a line 2210 for the upper jaw and a line 2212 for the lower jaw; in the frontal view along a line 2214 for the upper jaw and a line 2216 for the lower jaw. According to an embodiment of the present invention, this type of misalignment of upper and lower jaw planes (inertia system) due to one or more missing teeth can be corrected by excluding companion teeth of each missing tooth as illustrated in FIGS. 20A and 20B. The companion teeth for tooth 2204 are teeth 2304, 2302 and 2202. Tooth 2304 is the corresponding tooth in the upper jaw for tooth 2204. Teeth 2202 and 2302 are the corresponding teeth at the other side for the teeth 2304 and 2204. After excluding the companion teeth for the missing tooth 2204, the computed axes of inertia system 2206 for the upper jaw and inertia system 2208 for the lower jaw are back in parallel.

Figures 21A, 21B:
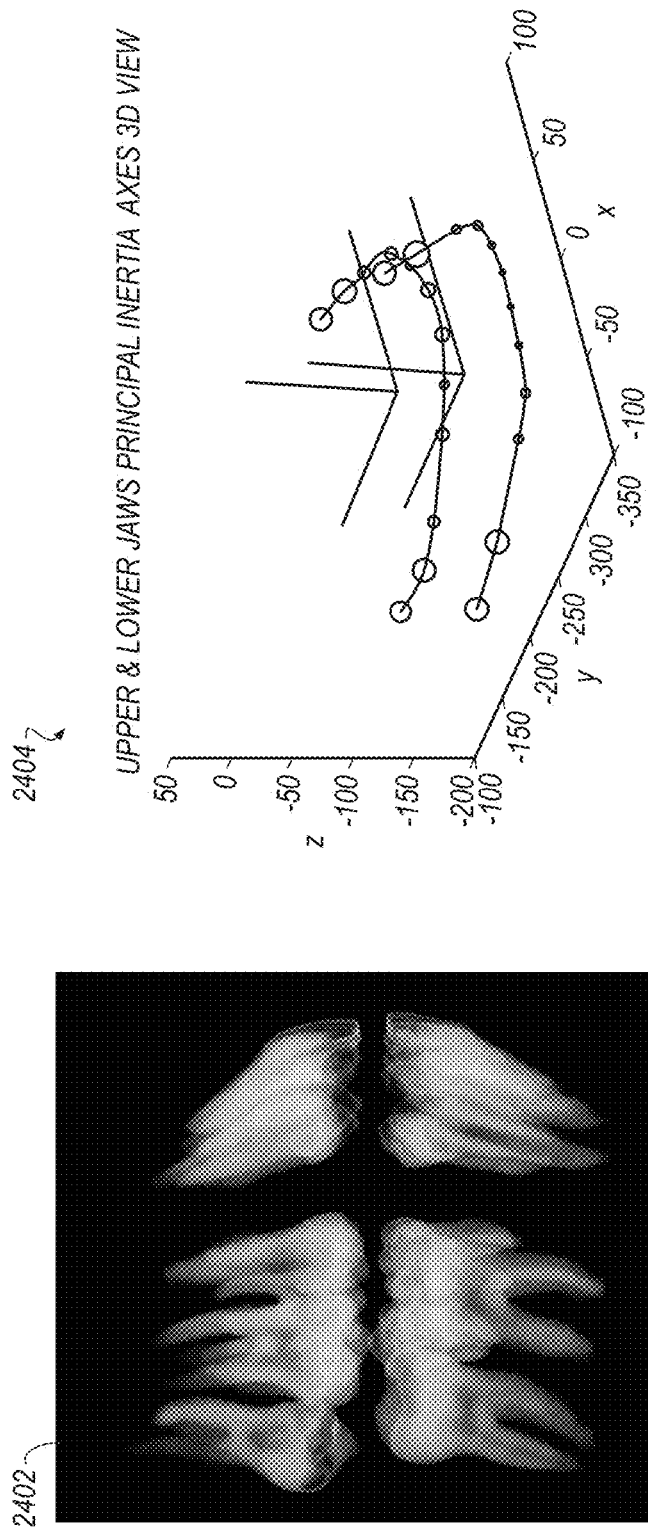
FIG. 21A is an example showing tooth exclusion for a missing tooth.
FIG. 21B is a graph showing computed axes of inertia systems for upper and lower jaws for the example of FIG. 21A.

FIGS. 21A and 21B illustrate segmented teeth from a CBCT volume in a case where companion teeth are excluded for a missing tooth. The segmentation results are shown in an image 2402. The computed axes of inertia systems for the upper and lower jaws are in parallel as demonstrated in a graph 2404.

Figure 22A:
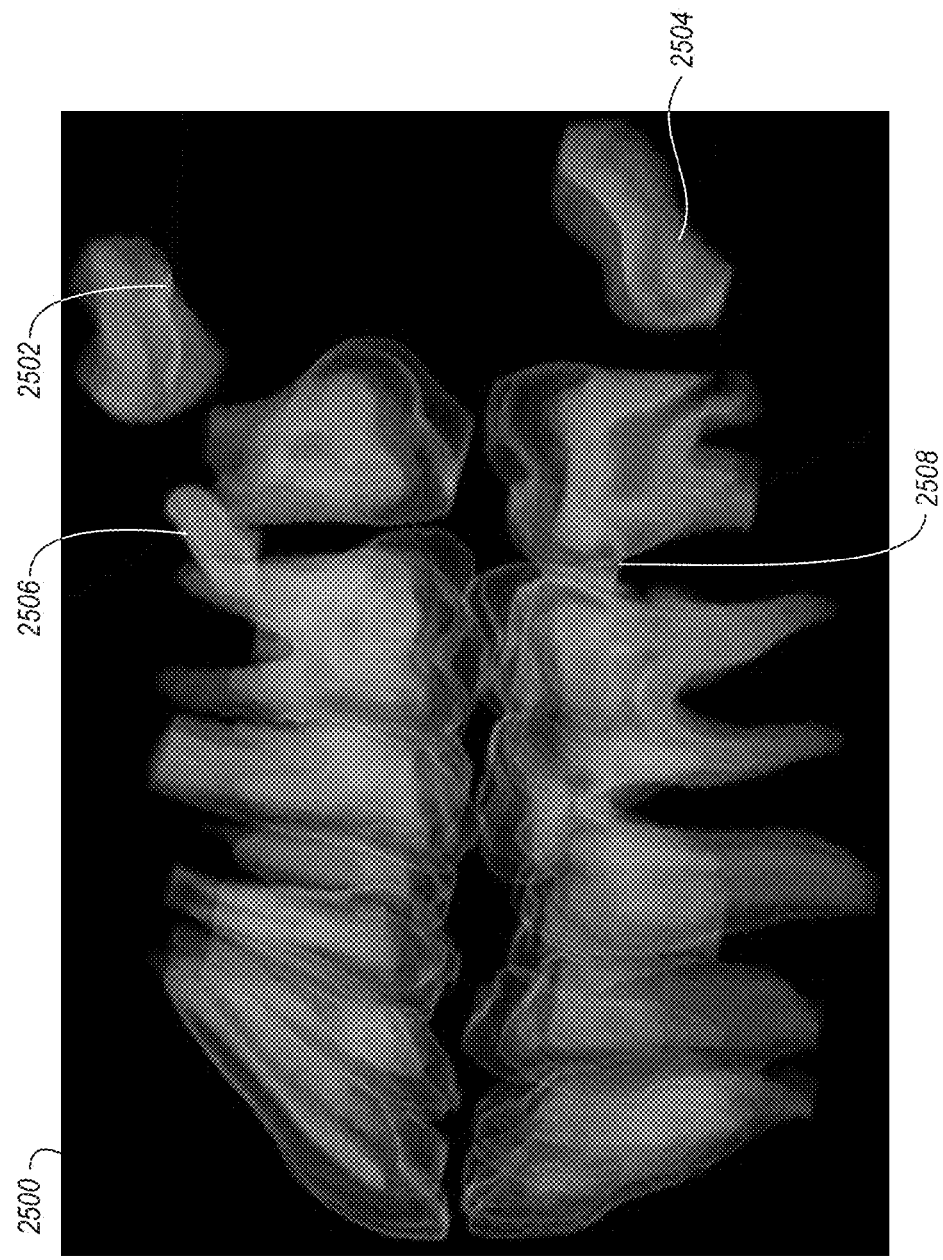
FIG. 22A is an example showing tooth exclusion for a missing tooth.
Figure 22B:
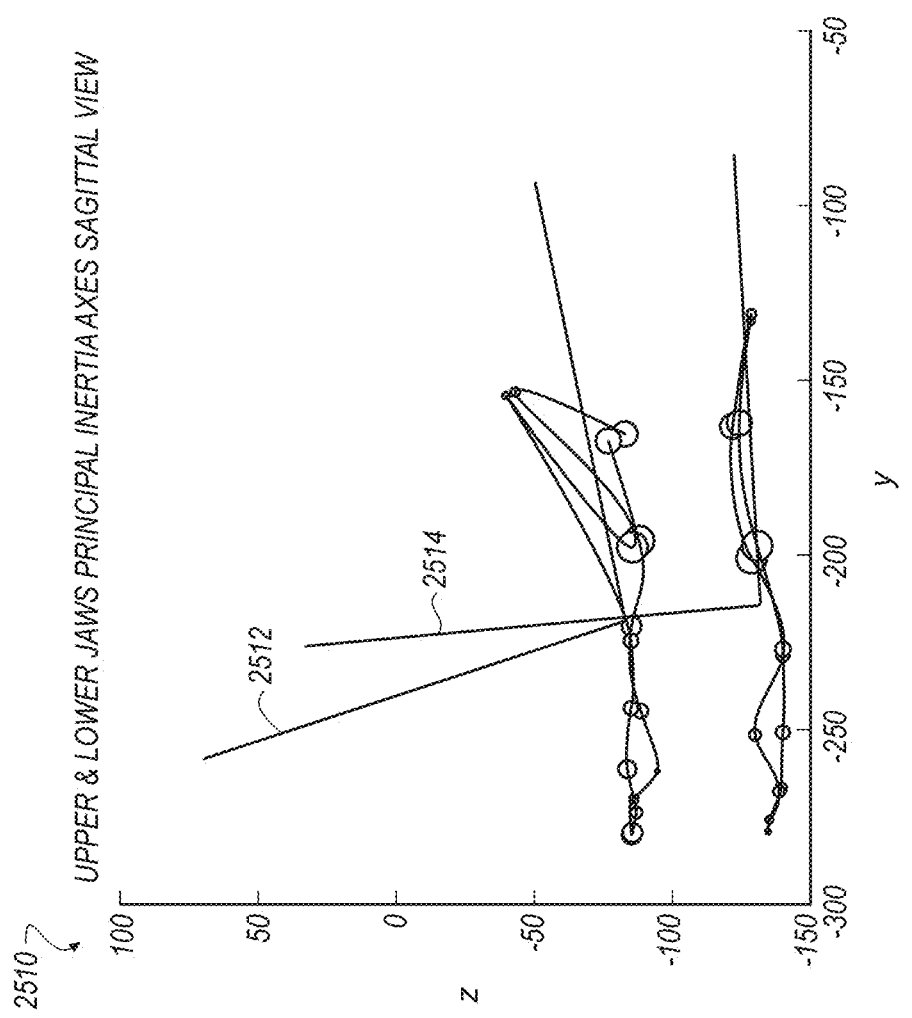
FIG. 22B is a graph showing computed axes of inertia systems for upper and lower jaws for the example of FIG. 22A.

FIGS. 22A and 22B show the method of exclusion of companion teeth applied to another patient using tooth exclusion step S124 (FIG. 2). As shown in an image 2500, teeth 2502, 2504, 2506 and 2508 are not fully developed. Their positioning, size, and orientation severely distort the physical properties of the upper jaw and lower jaw in terms of inertia system computation. A graph 2510 in FIG. 22B depicts the situation where upper jaw inertia system 2512 and lower jaw inertia system 2514 are severely misaligned (not in parallel).

Figure 23A:
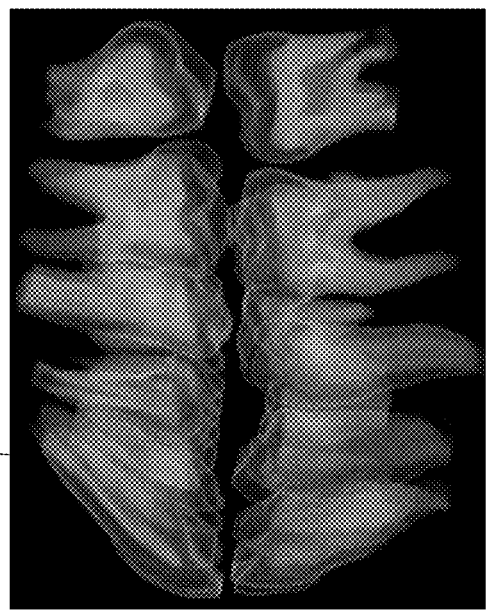
FIG. 23A is an image that shows the results of excluding specific teeth.
Figure 23B:
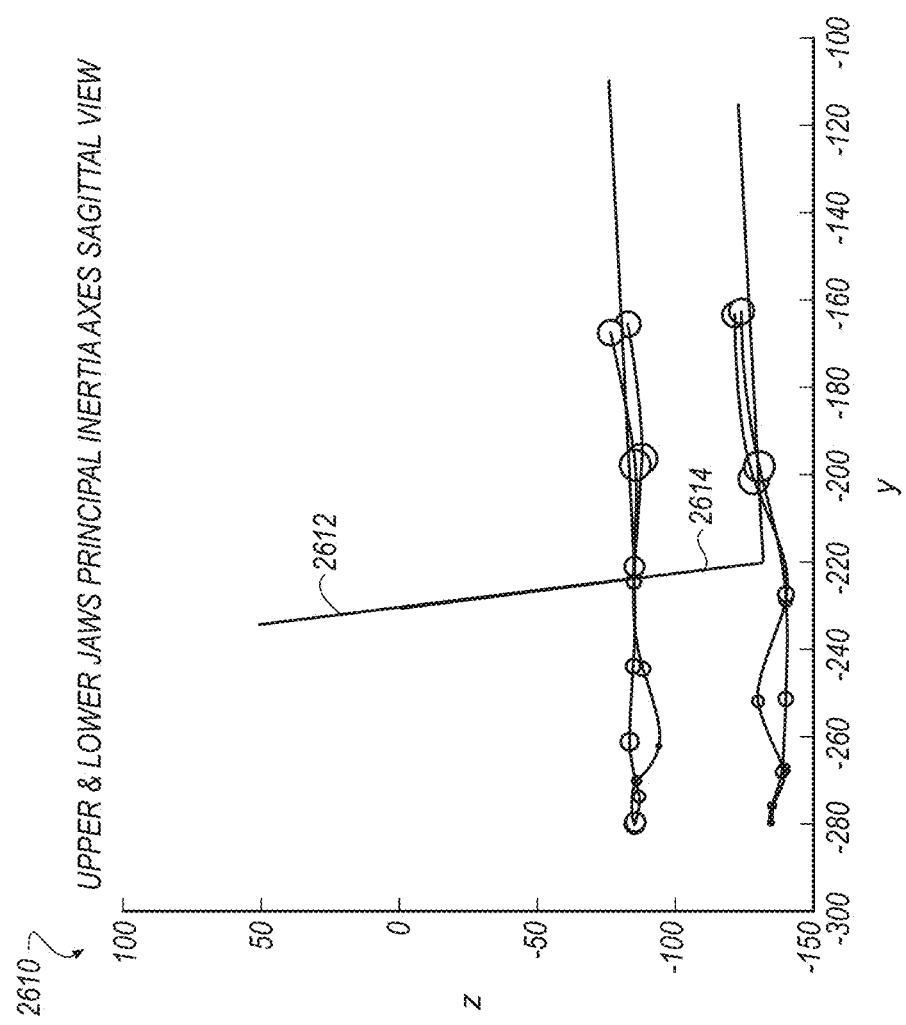
FIG. 23B is a graph showing computed axes of inertia systems for upper and lower jaws for the example of FIG. 23A.

FIGS. 23A and 23B show the results of excluding specific teeth from the image. An image 2600 shows the results of excluding teeth 2502, 2504, 2506 and 2508 from image 2500 of FIG. 22A. Without the disturbance of these teeth, the axes of inertia system 2612 of the upper jaw and inertia system 2614 lower jaw of the teeth shown in image 2600 are in parallel as depicted in a graph 2610.

According to an embodiment of the present invention, a computer program executes stored instructions that perform 3-D cephalometric analysis on image data accessed from an electronic memory in accordance with the method described. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to presently preferred embodiments, but it will be understood that variations and modifications can be effected that are within the scope of the invention. For example, the geometric primitive entered by the operator may have a default shape, such as a rectangle of a predefined size. Placement of the geometric primitive on the image display may be performed using gaze tracking or other mechanism, or may use a touch screen, or a pointer such as a computer mouse device. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for 3-D cephalometric analysis, the method executed at least in part by a computer, comprising:
   acquiring reconstructed volume image data from a computed tomographic scan of a patient's head;
   simultaneously displaying the acquired volume image data from at least a first 2-D view and a second 2-D view;
   for each of a plurality of anatomical features of the head:
   (i) accepting an operator instruction that positions a current 3D reference mark corresponding to the anatomical feature without naming the anatomical feature to reduce operator actions on one of the available 2-D views;
   (ii) displaying the current 3D reference mark on each of the at least first and second displayed 2-D views for location accuracy assessment in different views and adjusting the position of the current 3D reference mark in any of the at least first and second views, if needed for accuracy;
   (iii) subsequently naming the displayed current 3D reference mark representative of a particular anatomical feature using a model or learned data without added operator input;
   repeating steps (i) through (iii) to complete automatic naming of a plurality of positioned and displayed 3D reference marks;
   automatically segmenting upper and lower teeth;

deriving at least one cephalometric parameter according to the plurality of the positioned and named 3D reference marks and the segmented teeth;

displaying, storing, or transmitting the at least one derived cephalometric parameter;

determining a treatment plan for the patient based on the at least one derived cephalometric parameter; and performing treatment on the patient according to the determined treatment plan.

2. The method of claim 1 further comprising:

analyzing the 3D reference mark positioning from the operator instructions;

displaying an operator message recommending adjustment of the positioning; and accessing an operator adjustment instruction for adjusting the position of at least one of the current 3D reference marks according to the analyzing.

3. The method of claim 1 further comprising applying a 3-D tooth segmentation algorithm to the reconstructed volume image data.

4. The method of claim 3 further comprising displaying one or more reference planes generated according to teeth data segmented from an upper or a lower jaw.

5. The method of claim 4 further comprising displaying a jaw curve in one or more of the reference planes.

6. The method of claim 4 further comprising displaying, as a shape, a relative tooth mass for one or more teeth that are associated with the upper or lower jaw, wherein the relative tooth mass is indicated by one or more of the relative dimensions of the shape.

7. The method of claim 4 further comprising displaying one or more occlusal planes.

8. The method of claim 4 further comprising displaying one or more medial axes for teeth.

9. The method of claim 1 wherein accepting the operator instruction comprises responding to an operator instruction from a mouse or a touch screen entry.

10. The method of claim 1 further comprising identifying the anatomical feature corresponding to the positioned current 3D reference mark and displaying the name of the identified feature.

11. The method of claim 1 further comprising displaying the positioned current 3D reference mark on a third 2-D view that differs in perspective from the first and second 2-D views.

12. The method of claim 1 further comprising displaying an error prompt to the operator that indicates incorrect positioning of the current 3D reference mark.

13. The method of claim 1 further comprising displaying a listing of one or more reference marks for operator entry.

14. The method of claim 1 wherein the second 2-D view is substantially orthogonal to the first 2-D view.

15. The method of claim 1 further comprising displaying one or more reference planes generated according to one or more of the positioned and named 3D reference marks.

16. The method of claim 1 further comprising generating and displaying a digital phantom according to the positioned and named 3D reference marks.

17. A method for 3-D cephalometric analysis, the method executed at least in part by a computer and comprising:

acquiring reconstructed 3D volume image data from a computed tomographic scan of a patient's head;

simultaneously displaying the acquired volume image data from at least a first 2-D view and a second 2-D view that is substantially orthogonal to the first 2-D view;

for each of a plurality of anatomical features of the head:
  (i) accessing an operator instruction that positions a current 3D reference mark corresponding to the anatomical feature without naming the anatomical feature to reduce operator actions on one of the available views;
  (ii) displaying the current 3D reference mark on both of the at least first and second 2-D views for location accuracy assessment in different views;
  (iii) subsequently automatically identifying the displayed current 3D reference mark according to its position, and displaying an anatomical feature name that is associated with the current 3D reference mark without added operator input, wherein identifying the displayed current 3D reference mark comprises using a model or learned data;

automatically segmenting upper and lower teeth with one or more segmented teeth being excluded;

computing at least one 3D cephalometric parameter according to the plurality of the positioned and named 3D reference marks and the retained segmented teeth;

displaying, storing, or transmitting the at least one computed 3D cephalometric parameter for pathology diagnosis;

determining a treatment plan for the patient based on the at least one computed 3D cephalometric parameter; and performing treatment on the patient according to the determined treatment plan.

18. The method of claim 17 further comprising responding to an operator instruction by switching between the simultaneous display of the at least first and second 2-D views and a display of a single volume image in perspective.

19. The method of claim 17 further comprising accepting an operator entry that changes information related to one 3D reference mark.

20. The method of claim 17 further comprising displaying an indicator indicating a landmark that is to be positioned according to an entry by the operator.

* * * * *